US009907563B2

(12) United States Patent
Germain et al.

(10) Patent No.: US 9,907,563 B2
(45) Date of Patent: Mar. 6, 2018

(54) MEDICAL SYSTEMS AND METHODS

(71) Applicant: Boston Scientific Scimed, Inc., Maple Grove, MN (US)

(72) Inventors: Aaron Germain, San Jose, CA (US); Kyle Klein, San Jose, CA (US); Michael D. Walker, San Francisco, CA (US); Robin Bek, Campbell, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 697 days.

(21) Appl. No.: 14/247,649

(22) Filed: Apr. 8, 2014

(65) Prior Publication Data
US 2014/0303551 A1 Oct. 9, 2014

Related U.S. Application Data
(60) Provisional application No. 61/809,681, filed on Apr. 8, 2013.

(51) Int. Cl.
*A61B 17/32* (2006.01)
*A61B 17/22* (2006.01)
(Continued)

(52) U.S. Cl.
CPC ........ *A61B 17/22* (2013.01); *A61B 17/32002* (2013.01); *A61B 17/42* (2013.01);
(Continued)

(58) Field of Classification Search
CPC ................ A61B 17/42; A61B 18/1485; A61B 17/32002; A61B 2017/22079;
(Continued)

(56) References Cited

U.S. PATENT DOCUMENTS 4,261,360 A 4/1981 Perez
4,475,901 A * 10/1984 Kraegen ............. A61M 5/1723
604/66

(Continued)

FOREIGN PATENT DOCUMENTS

EP 1911391 A1 4/2008
EP 2100567 A1 9/2009
(Continued)

OTHER PUBLICATIONS

AAGL Practice Report: Practice Guidelines for the Management of Hysteroscopic Distending Media: (Replaces Hysteroscopic Fluid Monitoring Guidelines. J Am Assoc Gynecol Laparosc. 2000;7: 167-168) J Minim Invasive Gynecol. Mar.-Apr. 2013;20:137-48. doi: 10.1016/j.jmig.2012.12.002.
(Continued)

*Primary Examiner* — Son Dang
(74) *Attorney, Agent, or Firm* — Deager, Tufte & Wickhem, LLP

(57) ABSTRACT

A fluid management system for use in a tissue resection procedure includes a controller. An inflow pump is operated by the controller and configured to provide fluid inflow through a flow path to a site in patient's body. An outflow pump is operated by the controller and configured to provide fluid outflow through a flow path from the site in patient's body. A motor driven resecting device may be provided for resecting tissue at the site. The controller is configured to actuate an inflow pump and an outflow pump in response to various signals and various algorithms are provided to provide malfunction warnings and assure safe operation.

24 Claims, 22 Drawing Sheets

(51) Int. Cl.
*A61M 1/00* (2006.01)
*A61B 18/14* (2006.01)
*A61M 3/02* (2006.01)
*A61B 17/42* (2006.01)
*A61B 18/00* (2006.01)
*A61B 18/16* (2006.01)

(52) U.S. Cl.
CPC ......... *A61B 18/1485* (2013.01); *A61M 1/006* (2014.02); *A61M 1/0058* (2013.01); *A61M 3/0216* (2014.02); *A61B 2017/22079* (2013.01); *A61B 2017/4216* (2013.01); *A61B 2018/00196* (2013.01); *A61B 2018/00559* (2013.01); *A61B 2018/162* (2013.01); *A61B 2217/005* (2013.01); *A61B 2217/007* (2013.01); *A61M 2210/1433* (2013.01)

(58) Field of Classification Search
CPC ........... A61B 2018/00196; A61B 2018/00559; A61B 2217/005; A61B 2018/162; A61B 2017/4216; A61B 2217/007; A61M 1/0058; A61M 3/0216; A61M 1/006; A61M 2210/1433
See application file for complete search history.

(56) References Cited

U.S. PATENT DOCUMENTS

| | | |
|---|---|---|
| 4,650,462 A | 3/1987 | DeSatnick et al. |
| 4,735,603 A | 4/1988 | Goodson et al. |
| 5,098,375 A | 3/1992 | Baier |
| 5,106,364 A | 4/1992 | Hayafuji et al. |
| 5,213,571 A * | 5/1993 | Fujio ............... A61M 1/0058 604/22 |
| 5,277,696 A | 1/1994 | Hagen et al. |
| 5,382,229 A | 1/1995 | Grabenkort et al. |
| 5,437,629 A | 8/1995 | Goldrath |
| 5,599,301 A * | 2/1997 | Jacobs ............... A61M 25/1018 604/65 |
| 5,643,203 A | 7/1997 | Beiser et al. |
| 5,643,302 A * | 7/1997 | Beiser ............... A61B 1/00135 604/66 |
| 5,669,921 A | 9/1997 | Berman et al. |
| 5,730,752 A | 3/1998 | Alden et al. |
| 5,810,858 A | 9/1998 | Berman et al. |
| 5,823,990 A | 10/1998 | Henley et al. |
| 5,830,180 A | 11/1998 | Chandler et al. |
| 5,853,392 A | 12/1998 | Dennis |
| 5,906,615 A | 5/1999 | Thompson |
| 5,925,050 A | 7/1999 | Howard, III |
| 6,032,673 A | 3/2000 | Savage et al. |
| 6,052,060 A * | 4/2000 | Butler ............... H01F 27/402 336/55 |
| 6,109,268 A | 8/2000 | Thapliyal et al. |
| RE36,914 E | 10/2000 | Carlsen et al. |
| 6,159,160 A * | 12/2000 | Hsei ............... A61M 3/0283 600/560 |
| 6,206,014 B1 | 3/2001 | Cameron, III et al. |
| 6,245,084 B1 | 6/2001 | Mark et al. |
| 6,358,263 B2 | 3/2002 | Mark et al. |
| 6,629,986 B1 | 10/2003 | Ross et al. |
| 7,029,451 B2 | 4/2006 | Anderson et al. |
| 7,070,604 B1 | 7/2006 | Garito et al. |
| 7,204,821 B1 | 4/2007 | Clare et al. |
| 7,226,459 B2 | 6/2007 | Cesarini et al. |
| 7,384,417 B2 | 6/2008 | Cucin |
| 7,549,987 B2 | 6/2009 | Shadduck |
| 7,674,259 B2 | 3/2010 | Shadduck |
| 7,892,229 B2 | 2/2011 | Shadduck et al. |
| 8,313,485 B2 | 11/2012 | Shadduck |
| 8,512,326 B2 | 8/2013 | Shadduck et al. |
| 8,568,424 B2 * | 10/2013 | Shugrue ........... A61B 17/32002 606/119 |
| 8,728,066 B2 | 5/2014 | Shadduck et al. |
| 8,840,625 B2 | 9/2014 | Adams et al. |
| 8,840,626 B2 | 9/2014 | Adams et al. |
| 8,951,274 B2 | 2/2015 | Adams et al. |
| 2002/0010463 A1 | 1/2002 | Mulier et al. |
| 2002/0072745 A1 | 6/2002 | Truckai et al. |
| 2003/0060862 A1 | 3/2003 | Goble et al. |
| 2004/0049217 A1 | 3/2004 | Ross et al. |
| 2004/0092980 A1 | 5/2004 | Cesarini et al. |
| 2004/0102770 A1 | 5/2004 | Goble |
| 2004/0167427 A1 | 8/2004 | Quick et al. |
| 2004/0167428 A1 | 8/2004 | Quick et al. |
| 2004/0267255 A1 | 12/2004 | Auge, II et al. |
| 2005/0096649 A1 | 5/2005 | Adams |
| 2005/0236329 A1 | 10/2005 | Brotherton et al. |
| 2006/0047185 A1* | 3/2006 | Shener ............... A61B 1/00068 600/156 |
| 2006/0129091 A1* | 6/2006 | Bonnette ............... A61B 17/22 604/93.01 |
| 2006/0135955 A1 | 6/2006 | Shadduck |
| 2006/0200064 A1* | 9/2006 | Gross ............... A61M 1/16 604/5.01 |
| 2006/0224154 A1 | 10/2006 | Shadduck et al. |
| 2007/0016182 A1 | 1/2007 | Lipson et al. |
| 2007/0021713 A1 | 1/2007 | Kumar et al. |
| 2007/0036768 A1 | 2/2007 | Fraser et al. |
| 2007/0088275 A1 | 4/2007 | Stearns et al. |
| 2007/0244353 A1 | 10/2007 | Larsen |
| 2008/0039832 A1 | 2/2008 | Palanker et al. |
| 2008/0065060 A1 | 3/2008 | Ein-Gal |
| 2008/0091061 A1 | 4/2008 | Kumar et al. |
| 2008/0091071 A1 | 4/2008 | Kumar et al. |
| 2008/0097468 A1 | 4/2008 | Adams et al. |
| 2008/0097471 A1 | 4/2008 | Adams et al. |
| 2008/0097563 A1* | 4/2008 | Petrie ............... A61B 18/04 607/105 |
| 2008/0216827 A1* | 9/2008 | Seydel ............... A61J 15/0003 128/200.26 |
| 2008/0232977 A1* | 9/2008 | Pan ............... F04B 49/065 417/44.11 |
| 2008/0249366 A1* | 10/2008 | Gruber ............... A61B 1/303 600/154 |
| 2008/0249553 A1* | 10/2008 | Gruber ............... A61B 17/32002 606/171 |
| 2008/0287893 A1 | 11/2008 | Ineson |
| 2009/0030402 A1* | 1/2009 | Adahan ............... A61M 1/0066 604/540 |
| 2009/0043238 A1* | 2/2009 | Lane ............... A61B 5/0225 604/6.09 |
| 2009/0082715 A1 | 3/2009 | Charles |
| 2009/0137943 A1 | 5/2009 | Stearns et al. |
| 2009/0270897 A1 | 10/2009 | Adams et al. |
| 2009/0270898 A1 | 10/2009 | Chin et al. |
| 2009/0312753 A1 | 12/2009 | Shadduck |
| 2010/0100091 A1 | 4/2010 | Truckai |
| 2010/0152533 A1 | 6/2010 | Mark |
| 2010/0312054 A1* | 12/2010 | Beyar ............... A61B 1/00082 600/108 |
| 2011/0224486 A1 | 9/2011 | Nguyen et al. |
| 2011/0264090 A1 | 10/2011 | Shadduck et al. |
| 2011/0306968 A1 | 12/2011 | Beckman et al. |
| 2012/0053583 A1 | 3/2012 | Palanker et al. |
| 2012/0271300 A9 | 10/2012 | Shadduck et al. |
| 2012/0330292 A1 | 12/2012 | Shadduck et al. |
| 2013/0046304 A1 | 2/2013 | Germain et al. |
| 2013/0079702 A1 | 3/2013 | Klein et al. |
| 2013/0103021 A1 | 4/2013 | Germain et al. |
| 2013/0172805 A1 | 7/2013 | Truckai et al. |
| 2013/0172870 A1 | 7/2013 | Germain et al. |
| 2013/0211321 A1* | 8/2013 | Dubois ........... A61B 17/320708 604/26 |
| 2013/0231652 A1 | 9/2013 | Germain et al. |
| 2013/0296847 A1 | 11/2013 | Germain et al. |
| 2014/0012097 A1* | 1/2014 | McCrea ............... A61M 1/3679 600/301 |

(56) References Cited

U.S. PATENT DOCUMENTS

2014/0114238 A1* 4/2014 Lee .................... A61M 5/1456
  604/67

FOREIGN PATENT DOCUMENTS

| GB | 2327351 A | 1/1999 |
|----|-----------|--------|
| JP | 2002513614 A | 5/2002 |
| JP | 200473833 A | 3/2004 |
| WO | 2010096139 A2 | 8/2010 |
| WO | 2010096139 A3 | 12/2011 |
| WO | 2012017959 A1 | 2/2012 |

OTHER PUBLICATIONS

Liu, et al. Clinical application of hysteriscopic electroresection in 775 cases. Di YHi Jun Yi Da Xue Xue Bao. Apr. 2004;24(4):467-9. (in Chinese with English abstract).

Phillips, et al. The Effect of Dilute Vasopressin Solution on Blood Loss During Operative Hysteroscopy. J Am Assoc Gynecol Laparosc. Aug. 1996;3(4, Supplement):S38.

* cited by examiner

MEDICAL SYSTEMS AND METHODS

CROSS-REFERENCE TO RELATED APPLICATIONS

This application claims priority from U.S. Provisional Application 61/809,681, filed on Apr. 8, 2013, the full disclosure of which is incorporated herein by reference.

FIELD OF THE INVENTION

The present invention relates to surgical fluid management systems and methods, for example for use in distending the uterine cavity to allow resection and extraction of abnormal uterine tissue such as fibroids and polyps.

BACKGROUND OF THE INVENTION

Uterine fibroids are non-cancerous tumors that develop in the wall of uterus. Such fibroids occur in a large percentage of the female population, with some studies indicating up to 40 percent of all women have fibroids. Uterine fibroids can grow over time to be several centimeters in diameter and symptoms can include menorrhagia, reproductive dysfunction, pelvic pressure and pain.

One current treatment of fibroids is hysteroscopic resection or myomectomy which involves transcervical access to the uterus with a hysteroscope together with insertion of a resecting instrument through a working channel in the hysteroscope. The resecting instrument may be a mechanical tissue cutter or an electrosurgical resection device such as a cutting loop. Mechanical cutting devices are disclosed in U.S. Pat. Nos. 7,226,459; 6,032,673 and 5,730,752 and U.S. Published Patent Appl. 2009/0270898. An electrosurgical resecting device is disclosed in U.S. Pat. No. 5,906,615.

In a myomectomy or hysteroscopic resection, the initial step of the procedure includes distention of the uterine cavity to create a working space for assisting viewing through the hysteroscope. In a relaxed state, the uterine cavity collapses with the uterine walls in contact with one another. A fluid management system is used to distend the uterus to provide a working space wherein a fluid is administered through a passageway in the hysteroscope under sufficient pressure to expand or distend the uterine cavity. The fluids used to distend the uterus are typically liquid aqueous solutions such as a saline solution or a sugar-based aqueous solution.

In some RF electrosurgical resection procedures, the distending fluid is a non-conductive aqueous solution to limit RF current conduction.

One particular concern is the fact that fluid management systems typically administer the fluid under a pressure of up to 100 mm Hg or more which results in a significant risk that the distending fluid may be taken up by a cut blood vessel exposed in the uterine cavity. Such unwanted fluid uptake is known as intravasation, which can lead to serious complications and even death. For this reason, fluid management systems have been developed to monitor the patient's fluid uptake on a continuous basis during a procedure, typically using complicated systems that capture, collect and weigh distending fluids that flow through the uterine cavity.

While hysteroscopic resection can be effective in removing uterine fibroids, many commercially available instrument are too large in diameter and thus require anesthesia in an operating room environment. Conventional resectoscopes require cervical dilation to about 9 mm. What is needed is a system that can effectively resect and remove fibroid tissue through a small diameter hysteroscope.

SUMMARY OF THE INVENTION

In a first aspect of the present invention, a fibroid treatment system comprises a controller, an inflow pump operated by the controller and configured to provide fluid inflow through a flow path to a patient's uterine cavity, an outflow pump operated by the controller and configured to provide fluid outflow through a flow path to the uterine cavity and a motor driven resecting device operated by the controller. The resecting device comprises an elongate introducer member having a tissue extraction channel therein with a diameter of no less than 2.4 mm and an outer sleeve having a diameter of no more than 3.8 mm. Further, the resecting device is adapted to remove fibroid tissue at a rate of at least 2 gm/min. In one variation, the controller can be configured to actuate the inflow and outflow pumps in response to signals of fluid pressure in the uterine cavity and to maintain the target pressure as described above. Additionally, the signal of fluid pressure can be provided by a pressure sensor coupled to a static fluid column communicating with the uterine cavity. In another variation, the controller can be configured to operate the resecting device in response to at least one parameter selected from a group consisting of an inflow pump speed, an outflow pump speed and signals of fluid pressure in the uterine cavity as will be described further below.

In a second aspect of the invention, a fluid management system comprises a controller. A first pump is operated by the controller and configured to provide a fluid inflow to a site in patient's body. A second pump is also operated by the controller and configured to provide a fluid outflow from the site in patient's body. The controller is configured to maintain at least one operating parameter selected from a group consisting of a first pump speed, a fluid inflow rate, a second pump speed, and a fluid outflow rate, and the controller is configured to provide a fluid loss warning if the first pump speed exceeds a predetermined level for a pre-selected time interval.

In exemplary embodiments of the second aspect, the pre-selected time interval may be at least 1 second, at least 5 seconds, or at least 10 seconds. The controller may be further configured to de-activate at least one pump if the first pump speed exceeds the predetermined level for the pre-selected time interval, and the controller may be still further configured to de-activate a powered resecting device positioned in the site if the first pump speed exceeds the predetermined level for the pre-selected time interval.

In a third aspect of the present invention, a fluid management system comprises a controller. An inflow pump is operated by the controller and adapted to provide a fluid inflow through a flow path to a site in a patient's body. An outflow pump is also operated by the controller and adapted to provide a fluid outflow through a flow path from the site in the patient's body. The controller is configured to maintain at least one operating parameter selected from a group consisting of a first pump speed, a fluid inflow rate, a second pump speed, and a fluid outflow rate, and the controller is configured to provide a blocked flow warning if a calculated power for driving the inflow pump exceeds a predetermined level for a pre-selected time interval.

In exemplary embodiments of the third aspect of the present invention, the controller may be further configured to de-activate at least one pump if the calculated power for driving the inflow pump exceeds the predetermined level for the pre-selected time interval. The controller may be still further configured to de-activate a powered resecting device positioned in the site if the calculated power for driving the inflow pump exceeds the predetermined level for the pre-selected time interval.

In a fourth aspect of the present invention, a fluid management system comprises a controller. A first pump is operated by the controller and configured to provide fluid inflow to a site in patient's body. A second pump is also operated by the controller and configured to provide fluid outflow from the site in patient's body. The controller is configured to maintain at least one operating parameter selected from a group consisting of a first pump speed, a fluid inflow rate, a second pump speed, and a fluid outflow rate, and the controller is further configured to provide a blocked flow warning if an input voltage to the inflow pump motor is below a predetermined threshold voltage for a pre-selected time interval.

In exemplary embodiments of the fourth aspect of the present invention, the pre-selected time interval may range from 5 seconds to 120 seconds. The controller may be further configured to de-activate at least one pump if the input voltage to the inflow pump falls below the predetermined level for the pre-selected time interval, and the controller may be still further configured to de-activate the powered resecting device positioned in the site if the voltage to the inflow pump motor exceeds the predetermined level for the pre-selected time interval.

In a fifth aspect of the present invention, a fluid management system comprises a controller. An inflow pump is operated by the controller and configured to provide fluid inflow through a flow path to a site in patient's body. An outflow pump is also operated by the controller and configured to provide fluid outflow through a flow path from the site in patient's body. The controller is configured to maintain at least one operating parameter selected from a group consisting of a first pump speed, a fluid inflow rate, a second pump speed, and a fluid outflow rate, and the controller is further configured to provide a blocked flow warning if a measured current to the outflow pump exceeds a predetermined threshold voltage for a pre-selected time interval.

In a sixth aspect of the present invention, a fluid management system for use in a tissue resection procedure comprises a controller. An inflow pump is operated by the controller and configured to provide a fluid inflow through a flow path to a site in patient's body. An outflow pump is also operated by the controller and configured to provide a fluid outflow through a flow path from the site in patient's body. A motor driven resecting device for resecting tissue at the site is also provided. The controller is configured to actuate an inflow pump and an outflow pump in response to signals of actual pressure at the site in the patient's body to provide respective fluid inflow and fluid outflow to maintain a target pressure at the site, and the controller is further configured to de-activate the motor driven resecting device upon sensing that the actual pressure in the site falls below a predetermined threshold pressure level.

In exemplary embodiments of the sixth aspect of the present invention, the controller may be further configured to de-activate a motor in the motor driven resecting device if actual pressure in the site falls below a predetermined threshold pressure level. The controller may be alternatively configured to de-activate at least one tissue resecting electrode in the motor driven tissue resection device if actual pressure in the site falls below a predetermined threshold pressure level. The threshold pressure level is 100 mmHg or less, 50 mmHg or less, or 25 mmHg or less.

In a seventh aspect of the present invention, a fluid management system for use in tissue resection comprises a controller. The controller is configured to (a) actuate an inflow pump and an outflow pump in response to signals of actual pressure in a site in patient's body to thereby provide respective fluid inflows and fluid outflows to maintain a target pressure at said site, (b) send a tissue-engagement signal to the controller after sensing a predetermined increase in the actual pressure within a pre-selected interval resulting from a resecting tool engaging targeted tissue in the site, (c) send a tissue-disengagement signal to the controller after sensing a predetermined decrease in the actual pressure within a pre-selected interval resulting from a resecting tool subsequently disengaging from the tissue, and (d) modulate an operating parameter of the fluid management system in response to a tissue-engagement signal or a tissue-disengagement signal.

In exemplary embodiments of the seventh aspect of the present invention, the controller may be further configured to place the inflow pump in a ready state to provide a selected high inflow rate in response to a tissue-engagement signal. The controller may also be configured to actuate the inflow pump to provide a selected high inflow rate in response to a tissue dis-engagement signal.

DETAILED DESCRIPTION

Figure 1:
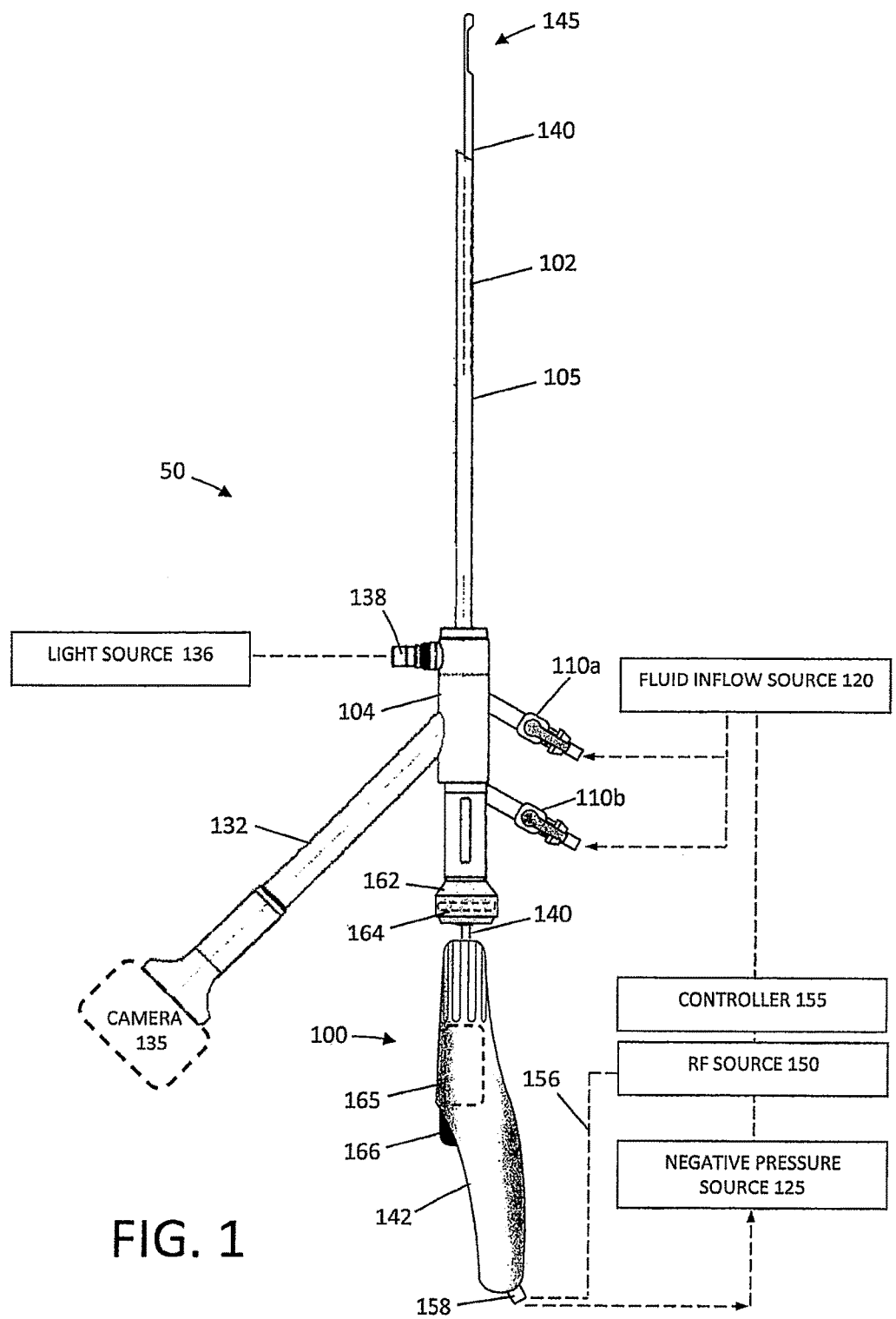
FIG. 1 is a plan view of an assembly including a hysteroscope and a tissue-resecting device corresponding to the invention that is inserted through the working channel of the hysteroscope.
Figure 2:
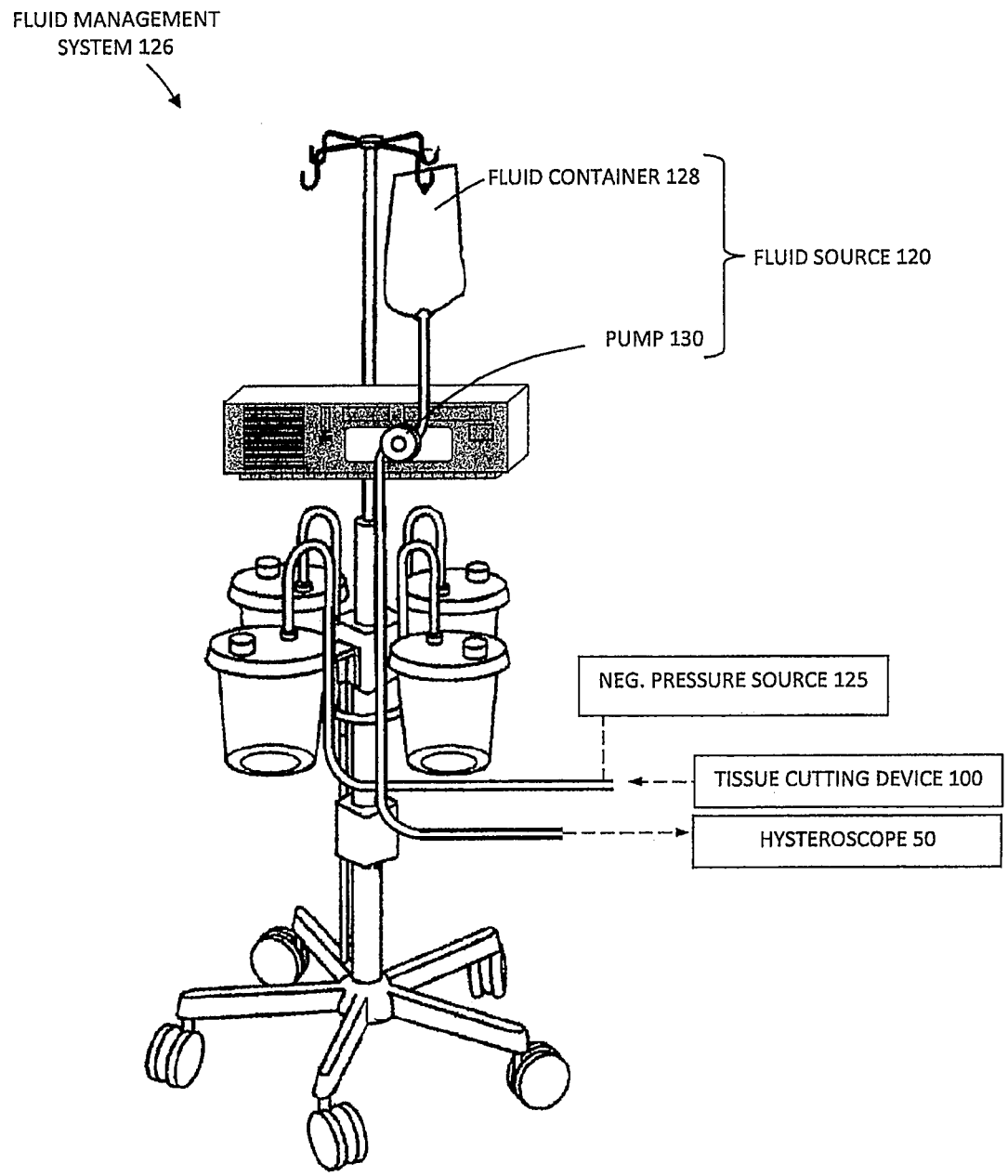
FIG. 2 is a schematic perspective view of a fluid management system used for distending the uterus and for assisting in electrosurgical tissue resection and extraction.

FIG. 1 illustrates an assembly that comprises an endoscope 50 used for hysteroscopy together with a tissue resecting device 100 extending through a working channel 102 of the endoscope. The endoscope or hysteroscope 50 has a handle 104 coupled to an elongated shaft 105 having a diameter of 5 mm to 7 mm. The working channel 102 therein may be round, D-shaped or any other suitable shape. The endoscope shaft 105 is further configured with an optics channel 106 and one or more fluid inflow/outflow channels 108a, 108b (FIG. 3) that communicate with valve-connectors 110a, 110b configured for coupling to a fluid inflow source 120 thereto, or optionally a negative pressure source 125 (FIGS. 1-2). The fluid inflow source 120 is a component of a fluid management system 126 as is known in the art (FIG. 2) which comprises a fluid container 128 and pump mechanism 130 which pumps fluid through the hysteroscope 50 into the uterine cavity. As can be seen in FIG. 2, the fluid management system 126 further includes the negative pressure source 125 (which can comprise an operating room wall suction source) coupled to the tissue-resecting device 100. The handle 104 of the endoscope includes the angled extension portion 132 with optics to which a videoscopic camera 135 can be operatively coupled. A light source 136 also is coupled to light coupling 138 on the handle of the hysteroscope 50. The working channel 102 of the hysteroscope is configured for insertion and manipulation of the tissue-resecting and extracting device 100, for example to treat and remove fibroid tissue. In one embodiment, the hysteroscope shaft 105 has an axial length of 21 cm, and can comprise a 0° scope, or 15° to 30° scope.

Still referring to FIG. 1, the tissue-resecting device 100 has a highly elongated shaft assembly 140 configured to extend through the working channel 102 in the hysteroscope. A handle 142 of the tissue-resecting device 100 is adapted for manipulating the electrosurgical working end 145 of the device. In use, the handle 142 can be manipulated both rotationally and axially, for example, to orient the working end 145 to resect targeted fibroid tissue. The tissue-resecting device 100 has subsystems coupled to its handle 142 to enable electrosurgical resecting of targeted tissue. A radiofrequency generator or RF source 150 and controller 155 are coupled to at least one RF electrode carried by the working end 145 as will be described in detail below. In one embodiment shown in FIG. 1, an electrical cable 156 and negative pressure source 125 are operatively coupled to a connector 158 in handle 142. The electrical cable couples the RF source 150 to the electrosurgical working end 145. The negative pressure source 125 communicates with a tissue extraction channel 160 in the shaft assembly 140 of the tissue extraction device 100 (FIG. 4).

FIG. 1 further illustrates a seal housing 162 that carries a flexible seal 164 carried by the hysteroscope handle 104 for sealing the shaft 140 of the tissue-resecting device 100 in the working channel 102 to prevent distending fluid from escaping from a uterine cavity.

In one embodiment as shown in FIG. 1, the handle 142 of tissue-resecting device 100 includes a motor drive 165 for reciprocating or otherwise moving a resecting component of the electrosurgical working end 145 as will be described below. The handle 142 optionally includes one or more actuator buttons 166 for actuating the device. In another embodiment, a footswitch can be used to operate the device. In one embodiment, the system includes a switch or control mechanism to provide a plurality of reciprocation speeds, for example 1 Hz, 2 Hz, 3 Hz, 4 Hz and up to 8 Hz. Further, the system can include a mechanism for moving and locking the reciprocating resecting sleeve in a non-extended position and in an extended position. Further, the system can include a mechanism for actuating a single reciprocating stroke.

Figure 4:
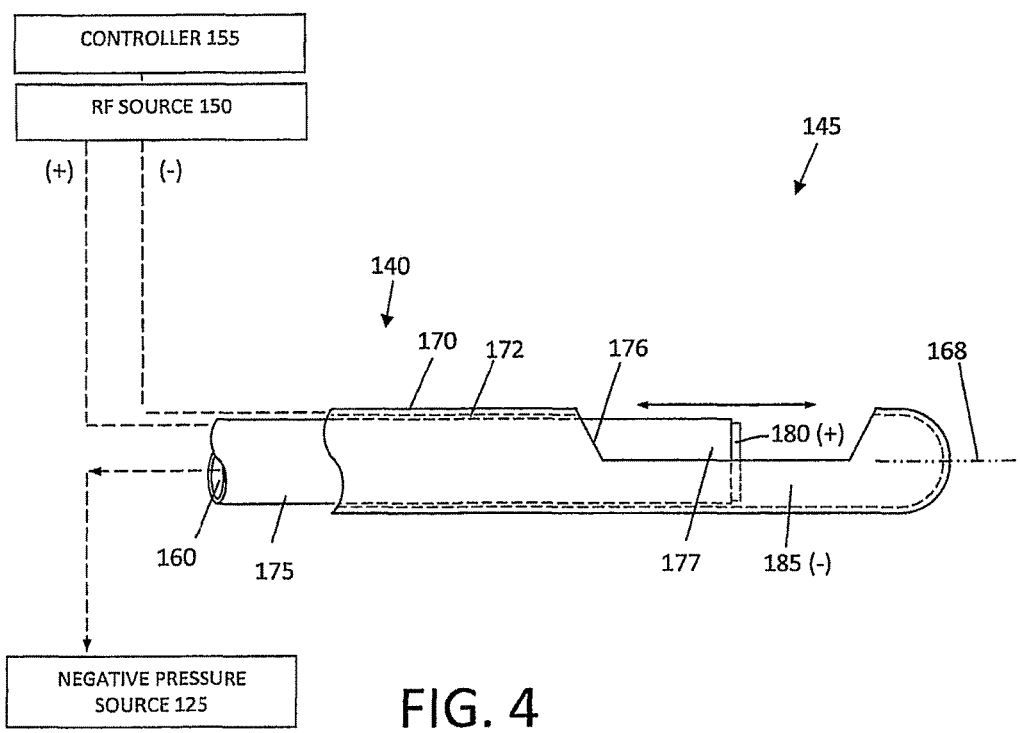
FIG. 4 is a schematic side view of the working end of the electrosurgical tissue-resecting device of FIG. 1 showing an outer sleeve and a reciprocating inner sleeve and an electrode arrangement.

Referring to FIGS. 1 and 4, an electrosurgical tissue resecting device has an elongate shaft assembly 140 extending about longitudinal axis 168 comprising an exterior or first outer sleeve 170 with passageway or lumen 172 therein that accommodates a second or inner sleeve 175 that can reciprocate (and optionally rotate or oscillate) in lumen 172 to resect tissue as is known in that art of such tubular cutters. In one embodiment, the tissue-receiving window 176 in the outer sleeve 170 has an axial length ranging between 10 mm and 30 mm and extends in a radial angle about outer sleeve 170 from about 45° to 210° relative to axis 168 of the sleeve. The outer and inner sleeves 170 and 175 can comprise a thin-wall stainless steel material and function as opposing polarity electrodes as will be described in detail below. FIGS. 6A-8 illustrate insulative layers carried by the outer and inner sleeves 170 and 175 to limits, control and/or prevent unwanted electrical current flows between certain portions go the sleeve. In one embodiment, a stainless steel outer sleeve 170 has an O.D. of 3.6 mm to 3.8 mm with an I.D. of 3.38 mm to 3.5 mm and with an inner insulative layer (described below) the sleeve has a nominal I.D. of about 3.175 mm". In this embodiment, the stainless steel inner sleeve 175 has an O.D. of about 3.05 mm with an I.D. of about 2.84 mm". The inner sleeve 175 with an outer insulative layer has a nominal O.D. of about 3.12 mm" to reciprocate in lumen 172. The inner diameters of the inner sleeve portions are described below. As can be seen in FIG. 4, the distal end 177 of inner sleeve 175 comprises a first polarity electrode with distal resecting electrode edge 180 about which plasma can be generated. The electrode edge 180 also can be described as an active electrode during tissue resecting since the electrode edge 180 then has a substantially smaller surface area than the opposing polarity or return electrode. In one embodiment in FIG. 4, the exposed surfaces of outer sleeve 170 comprises the second polarity electrode 185, which thus can be described as the return electrode since during use such an electrode surface has a substantially larger surface area compared to the functionally exposed surface area of the active electrode edge 180.

Figure 5:
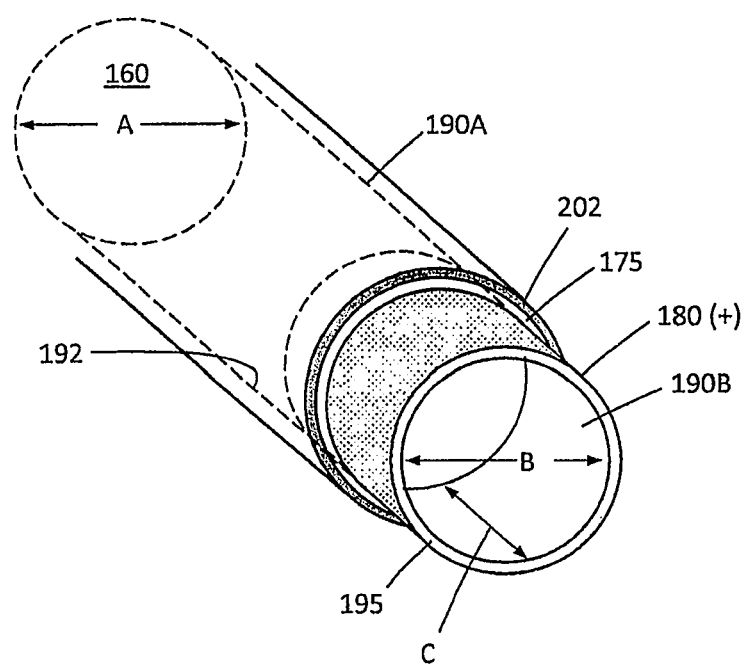
FIG. 5 is a schematic perspective view of the working end of the inner sleeve of FIG. 4 showing its electrode edge.
Figure 6A:
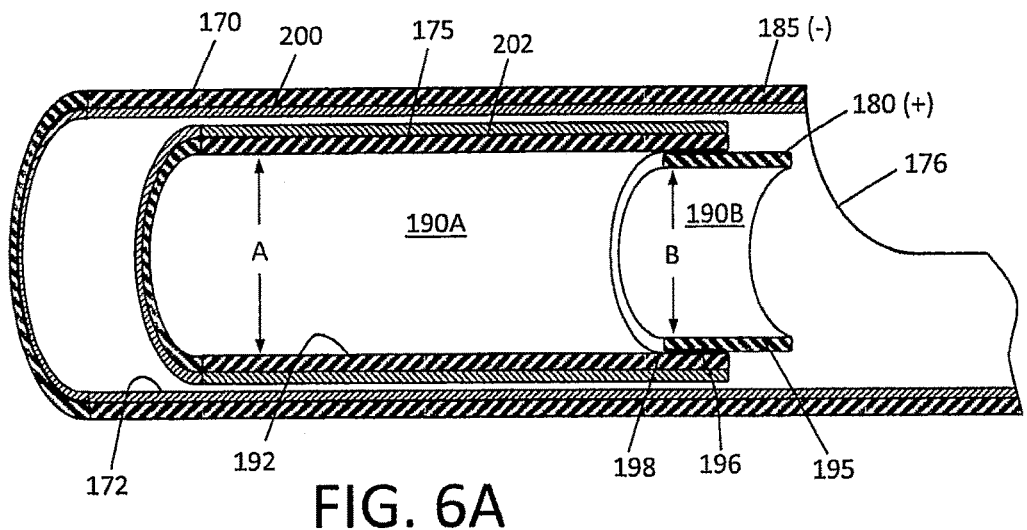
FIG. 6A is a schematic cut-away view of a portion of outer sleeve, inner RF resecting sleeve and a tissue-receiving window of the outer sleeve.

In one aspect of the invention, the inner sleeve or resecting sleeve 175 has an interior tissue extraction lumen 160 with first and second interior diameters that are adapted to electrosurgically resect tissue volumes rapidly—and thereafter consistently extract the resected tissue strips through the highly elongated lumen 160 without clogging. Now referring to FIGS. 5 and 6A, it can be seen that the inner sleeve 175 has a first diameter portion 190A that extends from the handle 142 (FIG. 1) to a distal region 192 of the sleeve 175 wherein the tissue extraction lumen transitions to a smaller second diameter lumen 190B with a reduced diameter indicated at B which is defined by the electrode sleeve element 195 that provides resecting electrode edge 180. The axial length C of the reduced cross-section lumen 190B can range from about 2 mm to 20 mm. In one embodiment, the first diameter A is between 2.8 mm and 2.9 mm and the second reduced diameter B is between 2.4 mm and 2.5 mm. As shown in FIG. 5, the inner sleeve 175 can be an electrically conductive stainless steel and the reduced diameter electrode portion also can comprise a stainless steel electrode sleeve element 195 that is welded in place by weld 196 (FIG. 6A). In another alternative embodiment, the electrode and reduced diameter electrode sleeve element 195 comprises a tungsten tube that can be press fit into the distal end 198 of inner sleeve 175. FIGS. 5 and 6A further illustrates the interfacing insulation layers 202 and 204 carried by the first and second sleeves 170, 175, respectively. In FIG. 6A, the outer sleeve 170 is lined with a thin-wall insulative material 200, such as PFA, or another material described below. Similarly, the inner sleeve 175 has an exterior insulative layer 202. These coating materials can be lubricious as well as electrically insulative to reduce friction during reciprocation of the inner sleeve 175.

The insulative layers 200 and 202 described above can comprise a lubricious, hydrophobic or hydrophilic polymeric material. For example, the material can comprise a bio-compatible material such as PFA, TEFLON®, polytetrafluroethylene (PTFE), FEP (Fluorinated ethylenepropylene), polyethylene, polyamide, ECTFE (Ethylenechlorotrifluoro-ethylene), ETFE, PVDF, polyvinyl chloride or silicone.

Figure 6B:
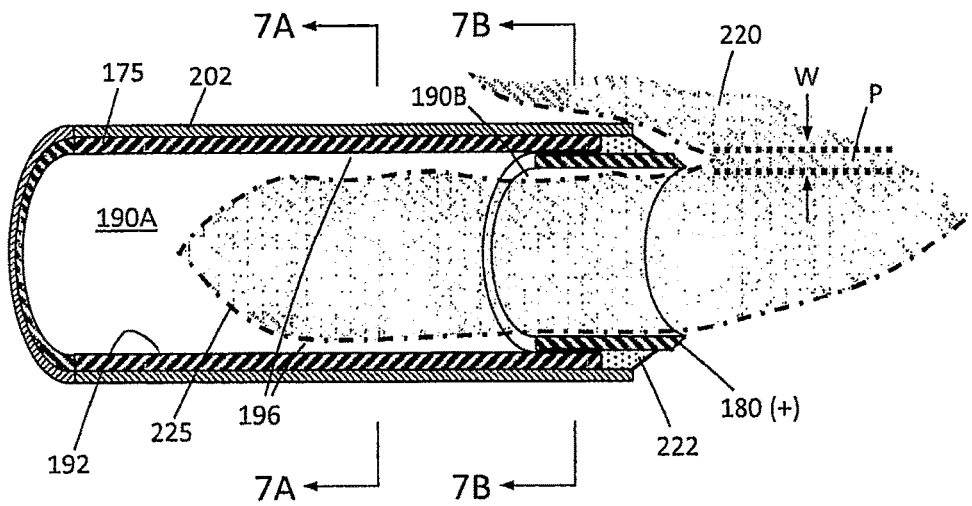
FIG. 6B is a schematic view of a distal end portion another embodiment of inner RF resecting sleeve.

Now turning to FIG. 6B, another variation of inner sleeve 175 is illustrated in a schematic view together with a tissue volume being resected with the plasma electrode edge 180. In this embodiment, as in other embodiments in this disclosure, the RF source operates at selected operational parameters to create a plasma around the electrode edge 180 of electrode sleeve 195 as is known in the art. Thus, the plasma generated at electrode edge 180 can resect and ablate a path P in the tissue 220, and is suited for resecting fibroid tissue and other abnormal uterine tissue. In FIG. 6B, the distal portion of the resecting sleeve 175 includes a ceramic collar 222 which is adjacent the distal edge 180 of the electrode sleeve 195. The ceramic 222 collar functions to confine plasma formation about the distal electrode edge 180 and functions further to prevent plasma from contacting and damaging the polymer insulative layer 202 on the resecting sleeve 175 during operation. In one aspect of the invention, the path P cut in the tissue 220 with the plasma at electrode edge 180 provides a path P having an ablated width indicated at W, wherein such path width W is substantially wide due to tissue vaporization. This removal and vaporization of tissue in path P is substantially different than the effect of cutting similar tissue with a sharp blade edge, as in various prior art devices. A sharp blade edge can divide tissue (without cauterization) but applies mechanical force to the tissue and may prevent a large cross section slug of tissue from being cut. In contrast, the plasma at the electrode edge 180 can vaporize a path P in tissue without applying any substantial force on the tissue to thus resect larger cross sections or slugs strips of tissue. Further, the plasma resecting effect reduces the cross section of tissue strip 225 received in the tissue-extraction lumen 190B. FIG. 6B depicts a tissue strip to 225 entering lumen 190B which has such a smaller cross-section than the lumen due to the vaporization of tissue. Further, the cross section of tissue 225 as it enters the larger cross-section lumen 190A results in even greater free space 196 around the tissue strip 225. Thus, the resection of tissue with the plasma electrode edge 180, together with the lumen transition from the smaller cross-section (190B) to the larger cross-section (190A) of the tissue-extraction lumen 160 can significantly reduce or eliminate the potential for successive resected tissue strips 225 to clog the lumen. Prior art resection devices with such small diameter tissue extraction lumen typically have problems with tissue clogging.

In another aspect of the invention, the negative pressure source 225 coupled to the proximal end of tissue extraction lumen 160 (see FIGS. 1 and 4) also assists in aspirating and moving tissue strips 225 in the proximal direction to a collection reservoir (not shown) outside the handle 142 of the device.

Figures 7A, 7B:
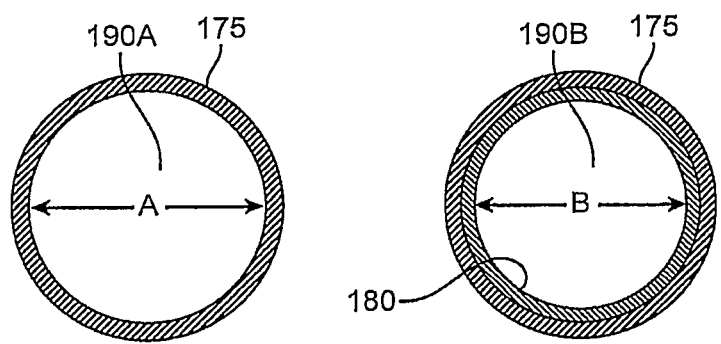
FIG. 7A is a cross sectional view of the inner RF resecting sleeve of FIG. 6B taken along line 7A-7A of FIG. 6B.
FIG. 7B is another cross sectional view of the inner RF resecting sleeve of FIG. 6B taken along line 7B-7B of FIG. 6B.
Figure 8:
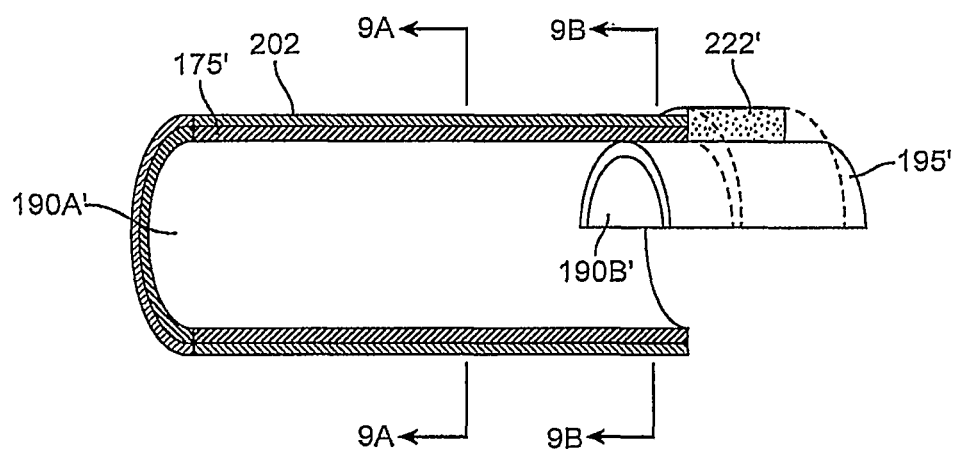
FIG. 8 is a schematic view of a distal end portion of another embodiment of inner RF resecting sleeve.
Figure 9A:
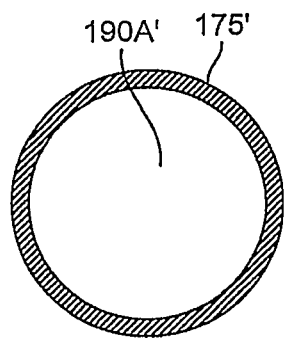
FIG. 9A is a cross sectional view of the RF resecting sleeve of FIG. 8 taken along line 9A-9A of FIG. 8.
Figure 9B:
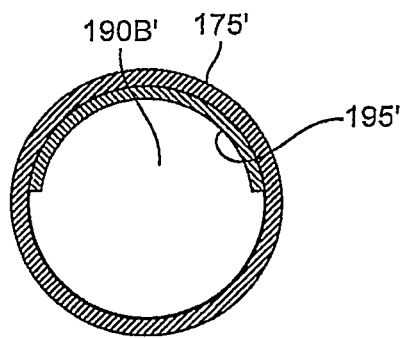
FIG. 9B is a cross sectional view of the RF resecting sleeve of FIG. 8 taken along line 9B-9B of FIG. 8.

FIGS. 7A-7B illustrate the change in lumen diameter of resecting sleeve 175 of FIG. 6B. FIG. 8 illustrates the distal end of a variation of resecting sleeve 175' which is configured with an electrode resecting element 195' that is partially tubular in contrast to the previously described tubular electrode element 195 (FIGS. 5 and 6A). FIGS. 9A-9B again illustrate the change in cross-section of the tissue extraction lumen between reduced cross-section region 190B' and the increased cross-section region 190A' of the resecting sleeve 175' of FIG. 8. Thus, the functionality remains the same whether the resecting electrode element 195' is tubular or partly tubular. In FIG. 8A, the ceramic collar 222' is shown, in one variation, as extending only partially around sleeve 175 to cooperate with the radial angle of resecting electrode element 195'. Further, the variation of FIG. 8 illustrates that the ceramic collar 222' has a larger outside diameter than insulative layer 202. Thus, friction may be reduced since the short axial length of the ceramic collar 222' interfaces and slides against the interfacing insulative layer 200 about the inner surface of lumen 172 of outer sleeve 170.

In general, one aspect of the invention comprises a tissue resecting and extracting device (FIGS. 10A-11C) that includes first and second concentric sleeves having an axis and wherein the second (inner) sleeve 175 has an axially-extending tissue extraction lumen therein, and wherein the second sleeve 175 is moveable between axially non-extended and extended positions relative to a tissue receiving window 176 in first sleeve 170 to resect tissue, and wherein the tissue extraction lumen 160 has first and second cross-sections. The second sleeve 175 has a distal end configured as a plasma electrode edge 180 to resect tissue disposed in tissue receiving window 176 of the first sleeve 170. Further, the distal end of the second sleeve, and more particularly, the electrode edge 180 is configured for plasma ablation of a substantially wide path in the tissue. In general, the tissue extraction device is configured with a tissue extraction lumen 160 having a distal end portion with a reduced cross-section that is smaller than a cross-section of medial and proximal portions of the lumen 160.

In one aspect of the invention, referring to FIGS. 7A-7B and 9A-9B, the tissue extraction lumen 160 has a reduced cross-sectional area in lumen region 190A proximate the plasma resecting tip or electrode edge 180 wherein said reduced cross section is less that 95%, 90%, 85% or 80% than the cross sectional area of medial and proximal portions 190B of the tissue extraction lumen, and wherein the axial length of the tissue extraction lumen is at least 10 cm, 20 cm, 30 cm or 40 cm. In one embodiment of tissue resecting device 100 for hysteroscopic fibroid resecting and extraction (FIG. 1), the shaft assembly 140 of the tissue resecting device is 35 cm in length.

Figure 10A:
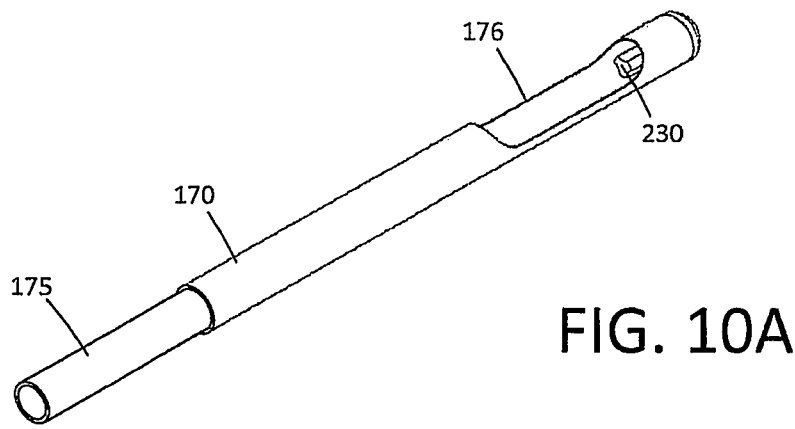
FIG. 10A is a perspective view of the working end of the tissue-resecting device of FIG. 1 with the reciprocating RF resecting sleeve in a non-extended position.
Figure 10B:
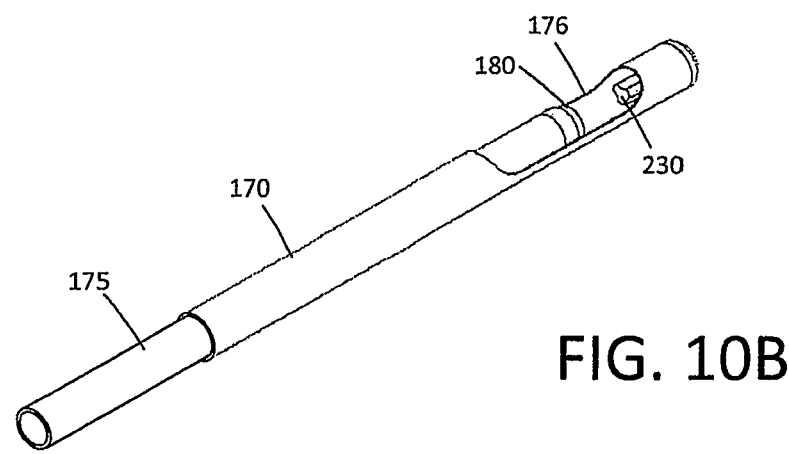
FIG. 10B is a perspective view of the tissue-resecting device of FIG. 1 with the reciprocating RF resecting sleeve in a partially extended position.
Figure 10C:
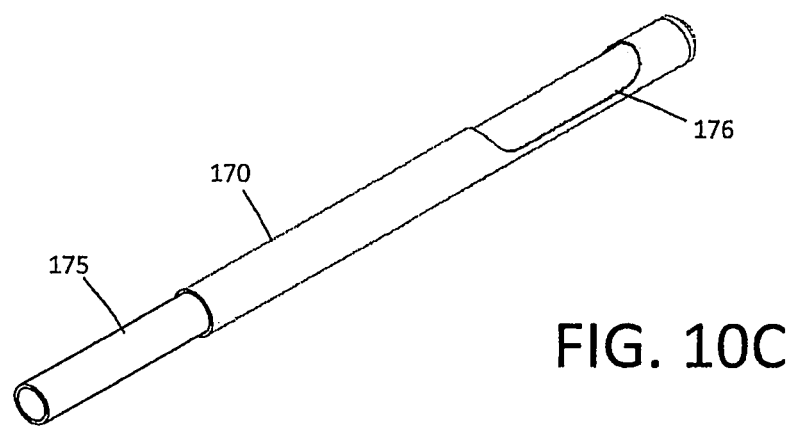
FIG. 10C is a perspective view of the tissue-resecting device of FIG. 1 with the reciprocating RF resecting sleeve in a fully extended position across the tissue-receiving window.
Figure 11A:
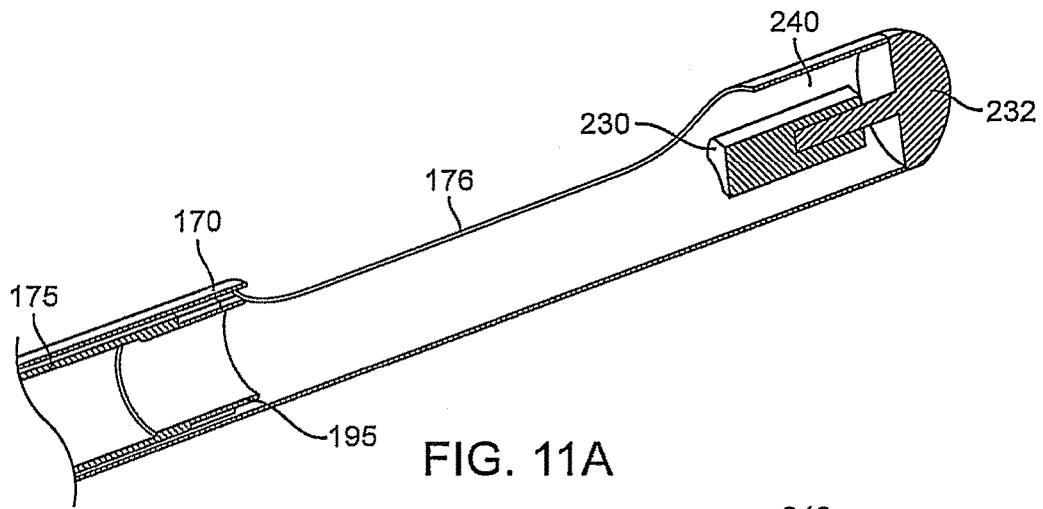
FIG. 11A is a sectional view of the working end of the tissue-resecting device of FIG. 10A with the reciprocating RF resecting sleeve in a non-extended position.
Figure 11B:
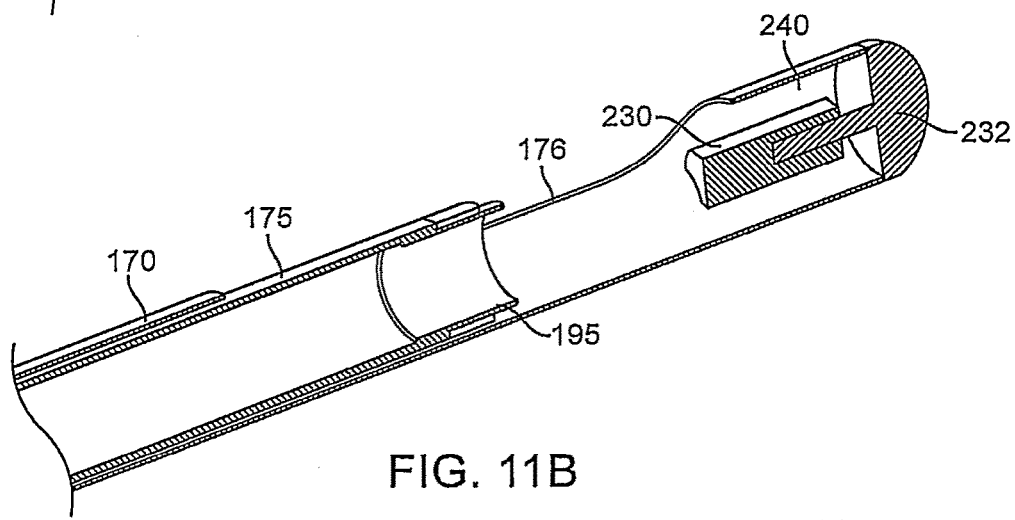
FIG. 11B is a sectional view of the working end of FIG. 10B with the reciprocating RF resecting sleeve in a partially extended position.
Figure 11C:
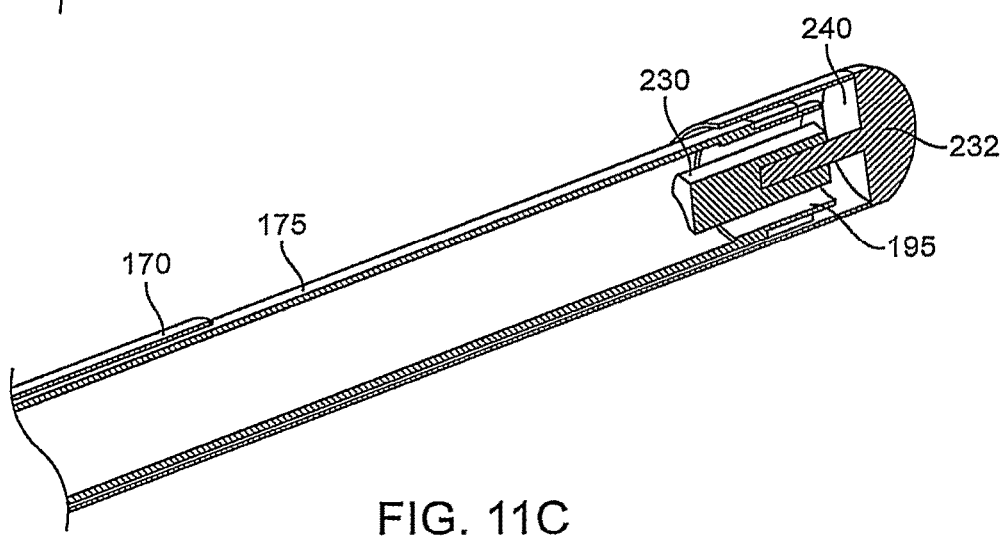
FIG. 11C is a sectional view of the working end of FIG. 10C with the reciprocating RF resecting sleeve in a fully extended position.

FIGS. 10A-10C illustrate the working end 145 of the tissue resecting device 100 with the reciprocating resecting sleeve or inner sleeve 175 in three different axial positions relative to the tissue receiving window 176 in outer sleeve 170. In FIG. 10A, the resecting sleeve 175 is shown in a retracted or non-extended position in which the sleeve 175 is at it proximal limit of motion and is prepared to advance distally to an extended position to thereby electrosurgically resect tissue positioned in and/or suctioned into in window 176. FIG. 10B shows the resecting sleeve 175 moved and advanced distally to a partially advanced or medial position relative to tissue resecting window 176. FIG. 10C illustrates the resecting sleeve 175 fully advanced and extended to the distal limit of its motion wherein the plasma resecting electrode 180 has extended past the distal end 226 of tissue receiving window 176 at which moment the resected tissue strip 225 in excised from tissue volume 220 and captured in reduced cross-sectional lumen region 190A.

Now referring to FIGS. 10A-10C and FIGS. 11A-11C, another aspect of the invention comprises "tissue displacement" mechanisms provided by multiple elements and processes to "displace" and move tissue strips 225 in the proximal direction in lumen 160 of resecting sleeve 175 to thus ensure that tissue does not clog the lumen of the inner sleeve 175. As can be seen in FIG. 10A and the enlarged views of FIGS. 11A-11C, one tissue displacement mechanism comprises a projecting element 230 that extends proximally from distal tip 232 which is fixedly attached to outer sleeve 170. The projecting element 230 extends proximally along central axis 168 in a distal chamber 240 defined by outer sleeve 170 and distal tip 232. In one embodiment depicted in FIG. 11A, the shaft-like projecting element 230, in a first functional aspect, comprises a mechanical pusher that functions to push a captured tissue strip 225 proximally from the small cross-section lumen 190B of resecting sleeve 175 as the resecting sleeve 175 moves to its fully advanced or extended position. In a second functional aspect, the chamber 240 in the distal end of sleeve 170 is configured to capture a volume of saline distending fluid 244 from the working space, and wherein the existing RF electrodes of the working end 145 are further configured to explosively vaporize the captured fluid 244 to generate proximally-directed forces on tissue strips 225 resected and disposed in lumen 160 of the resecting sleeve 175. Both of these two functional elements and processes (tissue displacement mechanisms) can apply a substantial mechanical force on the captured tissue strips 225 by means of the explosive vaporization of liquid in chamber 240 and can function to move tissue strips 225 in the proximal direction in the tissue extraction lumen 160. It has been found that using the combination of multiple functional elements and processes can virtually eliminate the potential for tissue clogging the tissue extraction lumen 160.

Figure 12A:
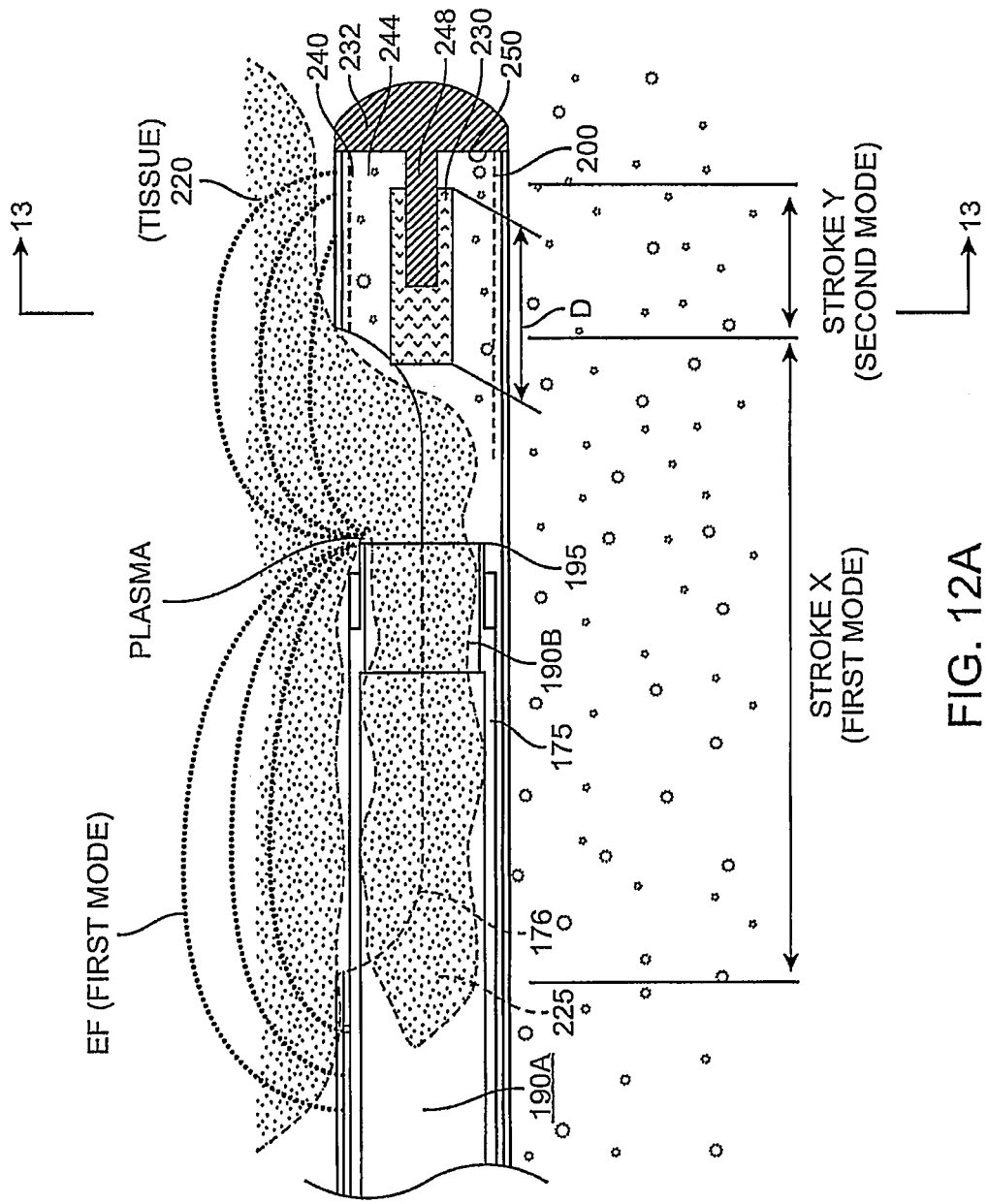
FIG. 12A is an enlarged sectional view of the working end of tissue-resecting device of FIG. 11B with the reciprocating RF resecting sleeve in a partially extended position showing the RF field in a first RF mode and plasma resecting of tissue.
Figure 12B:
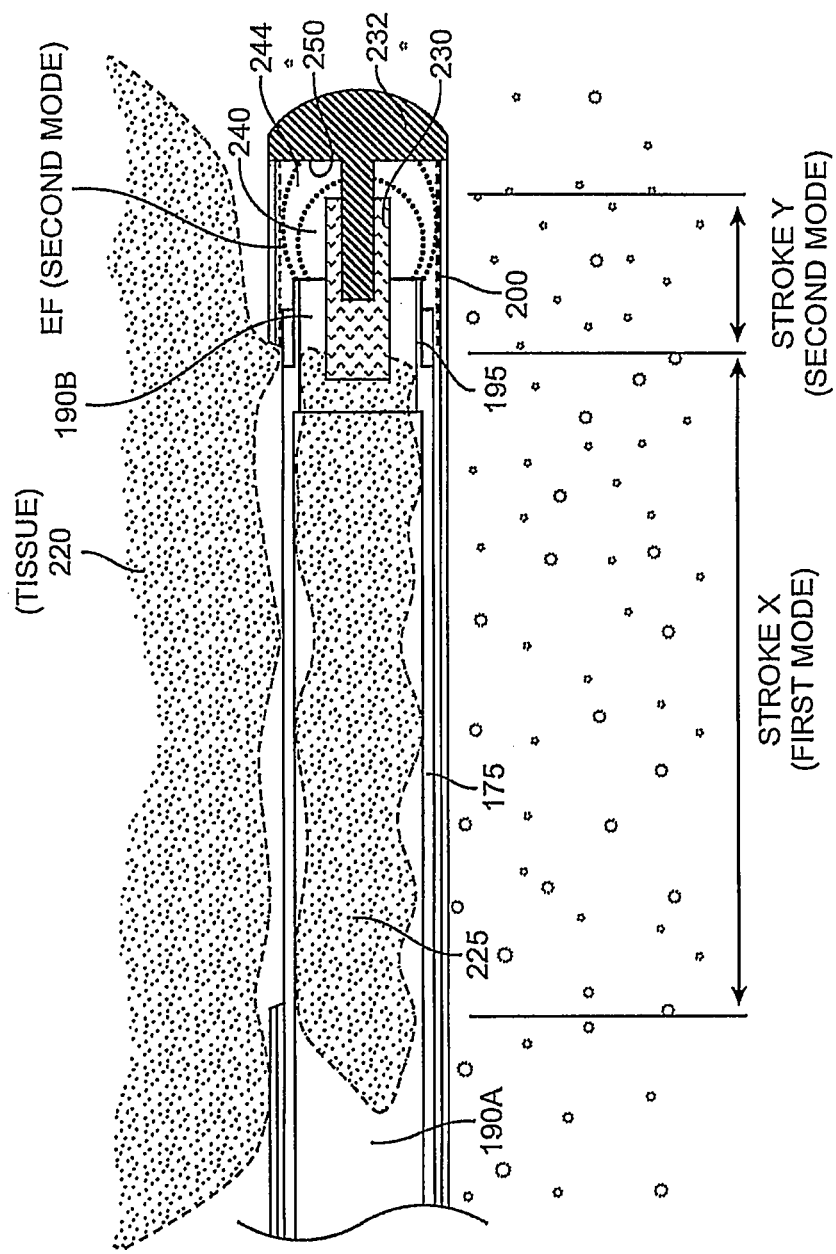
FIG. 12B is an enlarged sectional view of the working end of FIG. 11C with the reciprocating RF resecting sleeve almost fully extended and showing the RF fields switching to a second RF mode from a first RF mode shown in FIG. 12.
Figure 12C:
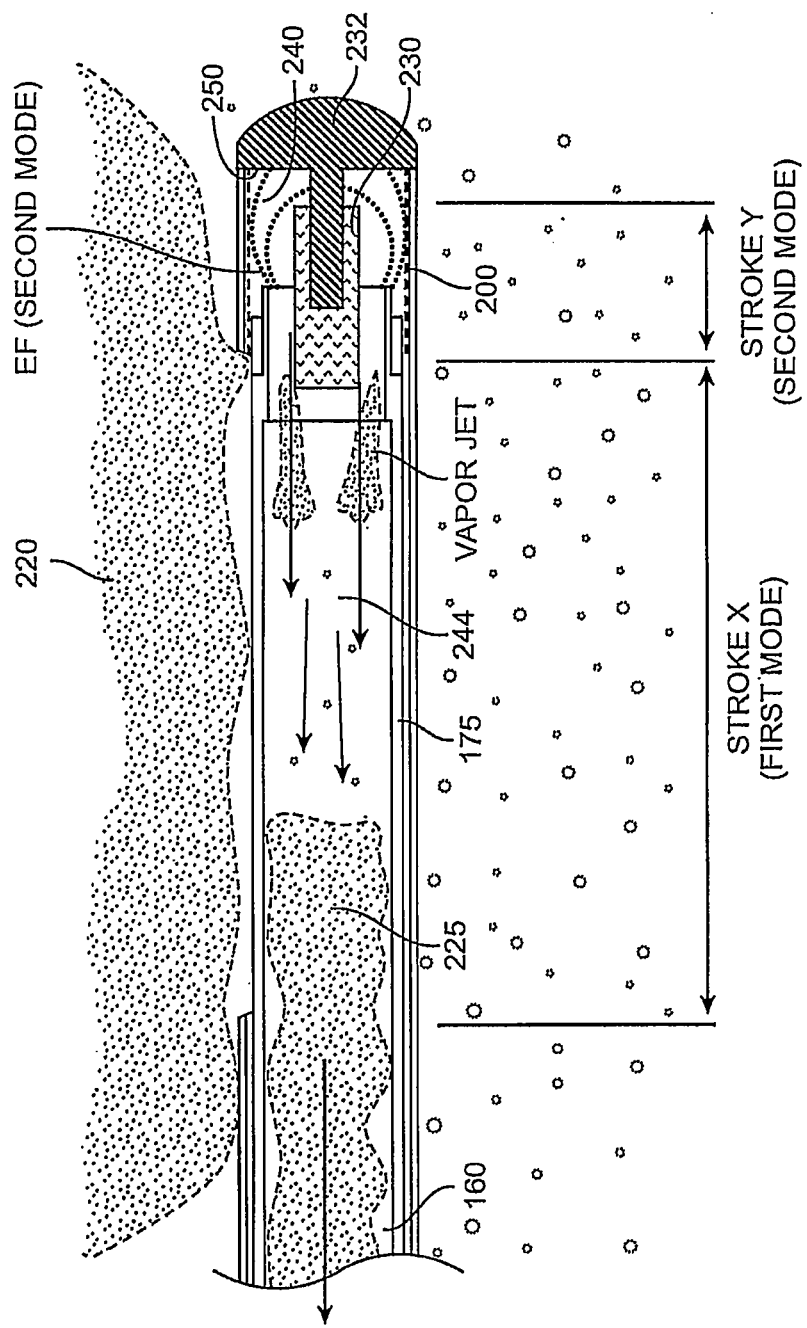
FIG. 12C is an enlarged sectional view of the working end of FIG. 11C with the reciprocating RF resecting sleeve again almost fully extended and showing the explosive vaporization of a captured liquid volume to expel resected tissue in the proximal direction.

More in particular, FIGS. 12A-12C illustrate sequentially the functional aspects of the tissue displacement mechanisms and the explosive vaporization of fluid captured in chamber 240. In FIG. 12A, the reciprocating resecting sleeve 175 is shown in a medial position advancing distally wherein plasma at the resecting electrode edge 180 is resecting a tissue strip 225 that is disposed within lumen 160 of the resecting sleeve 175. In FIG. 12A-12C, it can be seen that the system operates in first and second electrosurgical modes corresponding to the reciprocation and axial range of motion of resecting sleeve 175 relative to the tissue receiving window 176. As used herein, the term "electrosurgical mode" refers to which electrode of the two opposing polarity electrodes functions as an "active electrode" and which electrode functions as a "return electrode". The terms "active electrode" and "return electrode" are used in accordance with convention in the art—wherein an active electrode has a smaller surface area than the return electrode which thus focuses RF energy density about such an active electrode. In the working end 145 of FIGS. 10A-11C, the resecting electrode element 195 and its resecting electrode edge 180 must comprise the active electrode to focus energy about the electrode to generate the plasma for tissue resecting. Such a high-intensity, energetic plasma at the electrode edge 180 is needed throughout stroke X indicated in FIG. 12A-12B to resect tissue. The first mode occurs over an axial length of travel of inner resecting sleeve 175 as it crosses the tissue receiving window 176, at which time the entire exterior surface of outer sleeve 170 comprises the return electrode indicated at 185. The electrical fields EF of the first RF mode are indicated generally in FIG. 12A.

Figure 14:
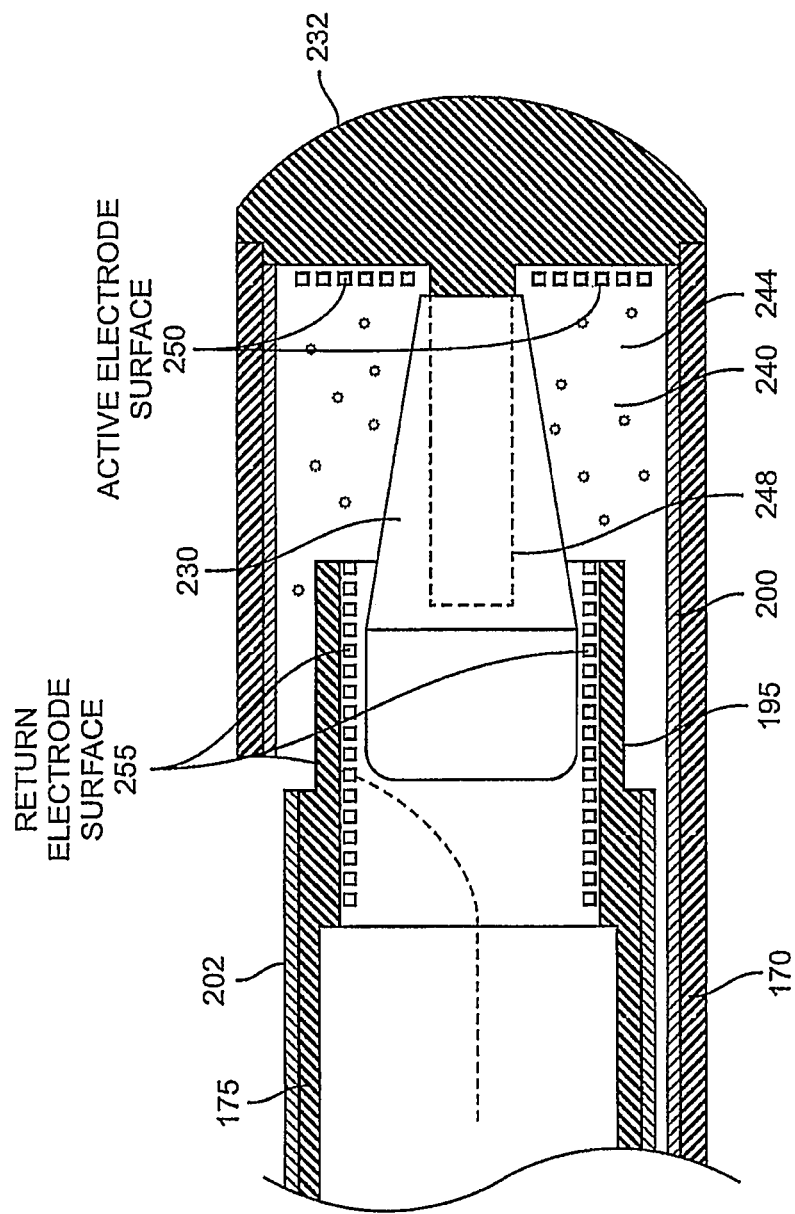
FIG. 14 is a sectional view of the working end of FIG. 12C showing an interior chamber and a variation of a projecting element.

FIG. 12 B illustrates the moment in time at which the distal advancement or extension of inner resecting sleeve 175 entirely crossed the tissue receiving window 176. At this time, the electrode sleeve 195 and its electrode edge 180 are confined within the mostly insulated-wall chamber 240 defined by the outer sleeve 170 and distal tip 232. At this moment, the system is configured to switch to the second RF mode in which the electric fields EF switch from those described previously in the first RF mode. As can be seen in FIG. 12B, in this second mode, the limited interior surface area 250 of distal tip 232 that interfaces chamber 240 functions as an active electrode and the distal end portion of resecting sleeve 175 exposed to chamber 240 acts as a return electrode. In this mode, very high energy densities occur about surface 250 and such a contained electric field EF can explosively and instantly vaporize the fluid 244 captured in chamber 240. The expansion of water vapor can be dramatic and can thus apply tremendous mechanical forces and fluid pressure on the tissue strip 225 to move the tissue strip in the proximal direction in the tissue extraction lumen 160. FIG. 12C illustrates such explosive or expansive vaporization of the distention fluid 244 captured in chamber 240 and further shows the tissue strip 225 being expelled in the proximal direction the lumen 160 of inner resecting sleeve 175. FIG. 14 further shows the relative surface areas of the active and return electrodes at the extended range of motion of the resecting sleeve 175, again illustrating that the surface area of the non-insulated distal end surface 250 is small compared to surface 255 of electrode sleeve which comprises the return electrode.

Still referring to FIGS. 12A-12C, it has been found that a single power setting on the RF source 150 and controller 155 can be configured both (i) to create plasma at the electrode resecting edge 180 of electrode sleeve 195 to resect tissue in the first mode, and (ii) to explosively vaporize the captured distention fluid 244 in the second mode. Further, it has been found that the system can function with RF mode-switching automatically at suitable reciprocation rates ranging from 0.5 cycles per second to 8 or 10 cycles per second. In trial, it has been found that the tissue resecting device described above can resect and extract tissue at the rate of from 2 grams/min to 8 grams/min without any potential for tissue strips 225 clogging the tissue extraction lumen 160. In one embodiment, a negative pressure source 125 can be coupled to the tissue extraction lumen 160 to apply tissue-extracting forces to tissue strips in the lumen.

Of particular interest, the fluid-capture chamber 240 defined by sleeve 170 and distal tip 232 can be designed to have a selected volume, exposed electrode surface area, length and geometry to optimize the application of expelling forces to resected tissue strips 225. In one embodiment, the diameter of the chamber is 3.175 mm and the length is 5.0 mm which taking into account the projecting element 230, provided a captured fluid volume of approximately 0.040 mL. In other variations, the captured fluid volume can range from 0.004 to 0.080 mL.

In one example, a chamber 240 with a captured liquid volume of 0.040 mL together with 100% conversion efficiency in an instantaneous vaporization would require 103 Joules to heat the liquid from room temperature to water vapor. In operation, since a Joule is a W*s, and the system reciprocate at 3 Hz, the power required would be on the order of 311 W for full, instantaneous conversion to water vapor. A corresponding theoretical expansion of 1700× would occur in the phase transition, which would results in up to 25,000 psi instantaneously (14.7 psi×1700), although due to losses in efficiency and non-instantaneous expansion, the actual pressures would be less. In any event, the pressures are substantial and can apply expelling forces sufficient to the expel the captured tissue strips 225 the length of the extraction channel in the probe.

Figure 13:
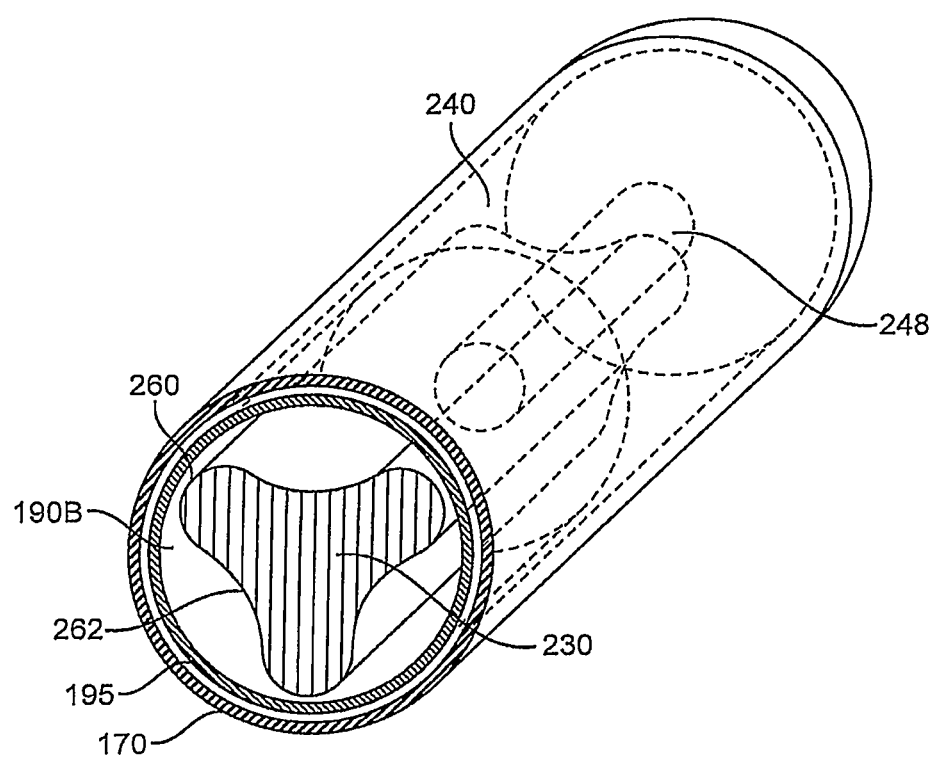
FIG. 13 is an enlarged perspective view of a portion of the working end of FIG. 12C showing an interior chamber and a fluted projecting element.

Referring to FIG. 12A, the interior chamber 240 can have an axial length from about 0.5 mm to 10 mm to capture a liquid volume ranging from about 0.004 mL to 0.010 mL. It can be understood in FIG. 12A, that the interior wall of chamber 240 has an insulator layer 200 which thus limits the electrode surface area 250 exposed to chamber 240. In one embodiment, the distal tip 232 is stainless steel and is welded to outer sleeve 170. The post element 248 is welded to tip 232 or machined as a feature thereof. The projecting element 230 in this embodiment is a non-conductive ceramic. FIG. 13 shows the cross-section of the ceramic projecting element 230 which is fluted, which in one embodiment has three flute elements 260 in three corresponding axial grooves 262 in its surface. Any number of flutes, channels or the like is possible, for example from 2 to about 20. The purpose of this design is to provide a significant cross-sectional area at the proximal end of the projecting element 230 to push the tissue strip 225, while at the same time the three grooves 262 permit the proximally-directed jetting of water vapor to impact the tissue exposed to the grooves 262. In one embodiment, the axial length D of the projecting element 230 is configured to push tissue entirely out of the reduced cross-sectional region 190B of the electrode sleeve element 195. In another embodiment, the volume of the chamber 240 is configured to capture liquid that when explosively vaporized provided a gas (water vapor) volume sufficient to expand into and occupy at least the volume defined by a 10% of the total length of extraction channel 160 in the device, at least 20% of the extraction channel 160, at least 40% of the extraction channel 160, at least 60% of the extraction channel 160, at least 80% of the extraction channel 160 or at least 100% of the extraction channel 160.

As can be understood from FIGS. 12A to 12C, the distention fluid 244 in the working space replenishes the captured fluid in chamber 240 as the resecting sleeve 175 moves in the proximal direction or towards its non-extended position. Thus, when the resecting sleeve 175 again moves in the distal direction to resect tissue, the interior chamber 240 is filled with fluid 244 which is then again contained and is then available for explosive vaporization as described above when the resecting sleeve 175 closes the tissue receiving window 176. In another embodiment, a one-way valve can be provided in the distal tip 232 to draw fluid directly into interior chamber 240 without the need for fluid to migrate through window 176.

Figure 15:
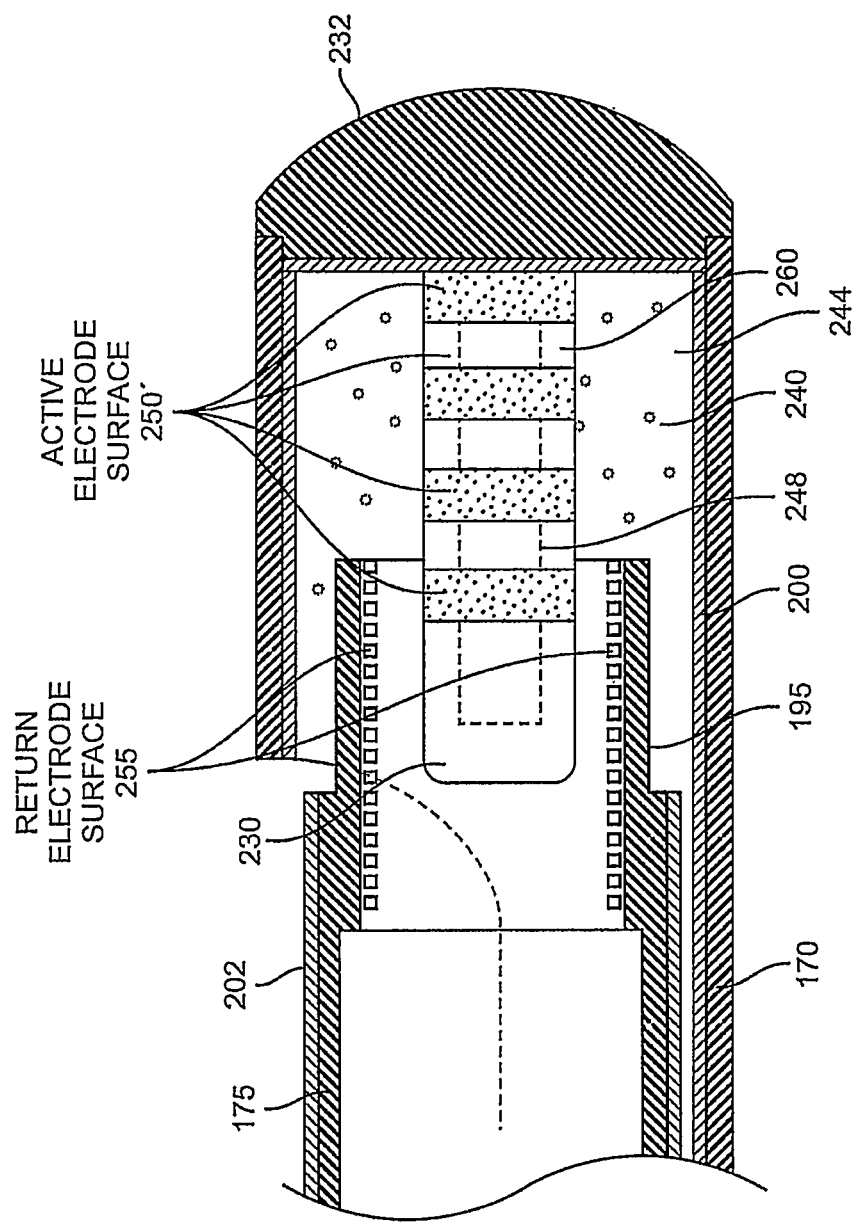
FIG. 15 is a sectional view of the working end of FIG. 12C showing an interior chamber and a variation of a projecting element configured to explosively vaporize the captured liquid volume.

FIG. 15 illustrates another variation in which the active electrode surface area 250' in the second mode comprises a projecting element 230 with conductive regions and non-conductive regions 260 which can have the effect of distributing the focused RF energy delivery over a plurality of discrete regions each in contact with the captured fluid 244. This configuration can more efficiently vaporize the captured fluid volume in chamber 240. In one embodiment, the conductive regions 250' can comprise metal discs or washers on post 248. In other variation (not shown) the conductive regions 250' can comprise holes, ports or pores in a ceramic material 260 fixed over an electrically conductive post 248.

In another embodiment, the RF source 150 and controller 155 can be programmed to modulate energy delivery parameters during stroke X and stroke Y in FIGS. 12A-12C to provide the optimal energy (i) for plasma resecting with electrode edge 180, and (ii) for explosively vaporizing the captured fluid in chamber 240. In one variation, the controller 155 can include an algorithm that activates the RF source 150 to delivery RF energy to working end as the resecting sleeve 175 moves in the distal direction towards its extended position to resect tissue but terminates RF energy delivery to the working end as the resecting sleeve 175 moves in the proximal direction towards its non-extended position. The termination of RF energy delivery during the proximal stroke of the resecting sleeve 175 eliminates energy delivery to electrode edge 180 when it is not resecting tissue which thus prevents unnecessary heating of distention fluid which would occur when RF energy is delivered during both the forward and backward strokes of the resecting sleeve.

Figure 16:
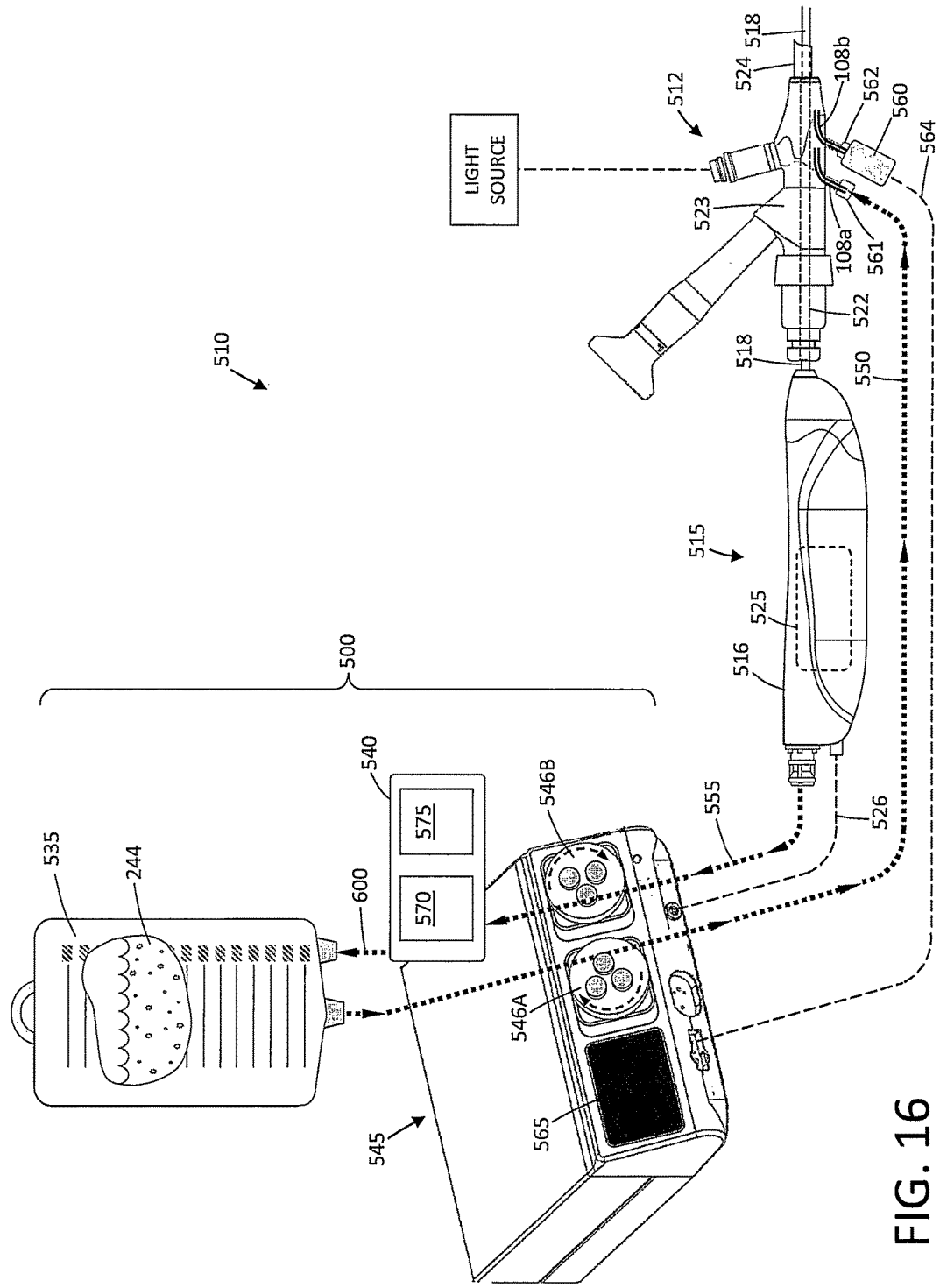
FIG. 16 is a schematic view of a system for fibroid removal including a fluid management system.
Figure 17:
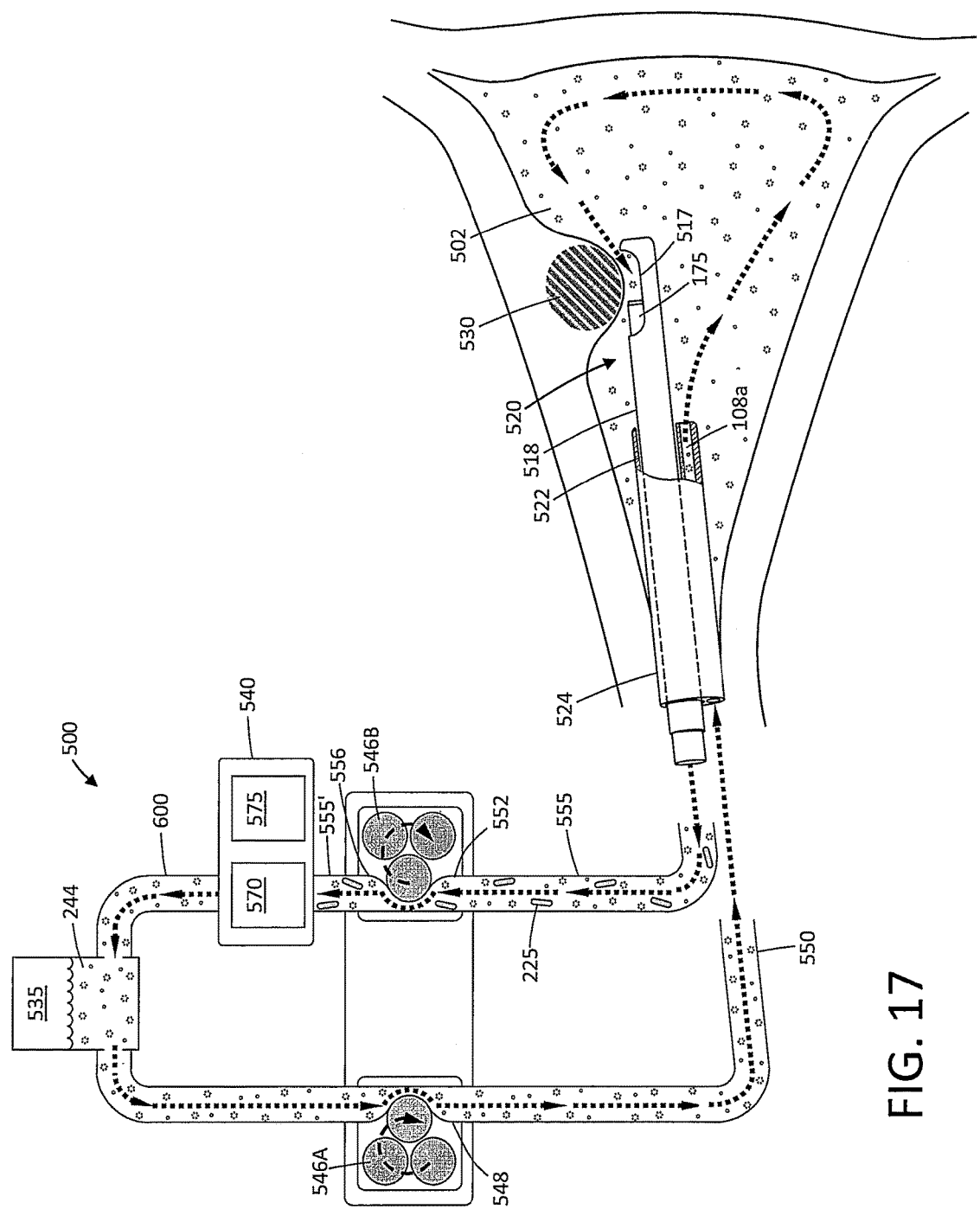
FIG. 17 is a schematic view of the fluid management system of FIG. 16 with an enlarged view of the working end of a tissue-resecting probe as generally described in FIGS. 1-12C in a position to resect and extract fibroid tissue.
Figure 18:
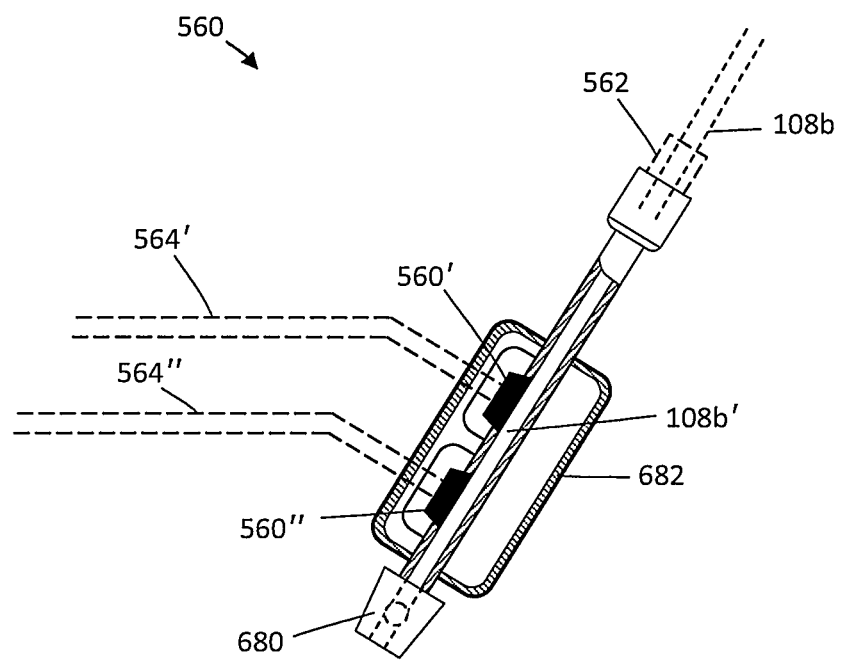
FIG. 18 is a schematic view of a pressure sensor component of the fluid management system of FIGS. 16-17.

FIGS. 16-18 illustrate a fluid management system 500 that can be used when treating tissue in a body cavity, space or potential space 502 (FIG. 17). The fluid management system 500 is depicted schematically in a hysteroscopic tissue resecting system 510 that is adapted for resecting and extraction of fibroids or other abnormal intra-uterine tissue using an endoscope or hysteroscope 512 and tissue resecting probe 515 that can be similar to those described above. FIG. 16 depicts the tissue resecting probe 515 with handle 516 and extending member including outer sleeve 518 with working end 520 (FIG. 17) that can be introduced through working channel 522 extending through the body 523 and shaft 524 of the hysteroscope 512. FIG. 16 further shows a motor 525 in handle 516 of the tissue resecting probe that is coupled to a controller and power supply by power cable 526. FIG. 17 illustrates the working end 520 of the resecting probe 515 in a uterine cavity proximate a targeted fibroid 530.

Referring to FIGS. 16-17, in general, the fluid management system 500 comprises a fluid source or reservoir 535 of a distention fluid 244, a controller and pump system to provide fluid inflows and outflows adapted to maintain distension of a body space and a filter system 540 for filtering distention fluid 244 that is removed from the body cavity and thereafter returned to the fluid source 535. The use of a recovered and filtered fluid 244 and the replenishment of the fluid source 535 is advantageous because (i) the closed-loop fluid management system can effectively measure fluid deficit to thereby monitor intravasation and insure patient safety, (ii) the system can be set up and operated in a very time-efficient manner, and (ii) the system can be compact and less expensive to thereby assist in enabling office-based procedures.

Figure 3:
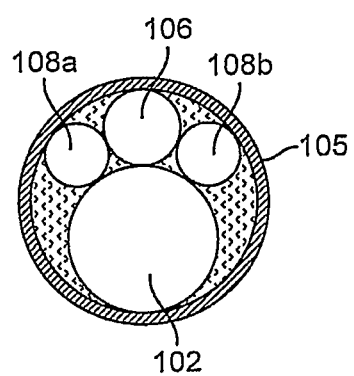
FIG. 3 is a cross-sectional view of the shaft of the hysteroscope of FIG. 1 showing various channels therein.

The fluid management system 500 (FIG. 16) includes a computer control system that is integrated with the RF control system in an integrated controller 545. The controller 545 is adapted to control first and second peristaltic pumps 546A and 546B for providing inflows and outflows of a distention fluid 244, such as saline solution, from source 535 for the purpose of distending the body cavity. The first peristaltic pump may also be called an inflow pump or infusion pump herein. The second peristaltic pump may also be called an outflow pump or aspiration pump herein. The controller 545 and control algorithms are adapted to control the intra-cavity pressure during a tissue resecting and extracting procedure as depicted in FIG. 17. In one embodiment shown in FIGS. 16-18, the controller 545 controls the inflow pump 546A to provide positive pressure at the outflow side 548 of the pump (FIG. 17) to provide inflows of distention fluid 244 through inflow line 550 which is in communication with fitting 561 and fluid flow channel 108a in hysteroscope 515. The flow channel 108a is described above in a previous embodiment and is illustrated in FIG. 3 above. The controller 545 further controls the outflow pump 546B to provide negative pressure to the outflow line 555 at the inflow side 552 of the pump (FIG. 17) to provide outflows of distention fluid 244 from the body cavity 502. As described above, the explosive vaporization of fluid in the working end 525 of resecting probe 515 functions to expel tissue strips 225 proximally in the extraction channel 160 of resecting sleeve 175, which can operate in conjunction with negative pressure in line 555 provided by pump 546B. In operation, the outflow pump 546B also operates to provide positive pressure on the outflow side 556 of pump 546B in the second outflow line portion 555' to pump outflows of distention fluid 244 through the filter system 540 and back to the fluid source 535.

In one system embodiment, the controller 545 operates to control pressure in cavity 502 by pressure signals from a pressure sensor 560 that is coupled to a fitting 562 in hysterocope 512 which communicates with a flow channel 108b (see FIG. 16) that extends through the hysteroscope. In one embodiment, the flow channel 108b has a diameter of at least 1.0 mm to allow highly accurate sensing of actual intra-cavity pressure. In prior art commercially-available fluid management systems, the intra-cavity pressure is typically estimated by various calculations using known flow rates through a pump or remote pressure sensors in the fluid inflow line that can measure back pressures. Such prior art fluid management systems are stand-alone systems and are adapted for use with a wide variety of hysteroscopes and endoscopes, most of which do not have a dedicated flow channel for communicating with a pressure sensor. For this reason, prior art fluid management systems rely on algorithms and calculations to only estimate intra-cavity pressure.

In one embodiment, as depicted in FIG. 16, the pressure sensor 560 is disposable and is detachably coupled to the endoscope 512 and is in fluid communication with the body cavity through a flow channel 108b in the endoscope. The pressure sensor 560 is operatively coupled to controller 545 by cable 564. The pressure sensor can be a biocompatible, piezoresistive silicon sensor of the type used in invasive blood pressure monitoring. For example, the sensor can be a piezoresistive silicon pressure sensor, Model No. 1620, available from Measurement Specialties. Ltd., 45738 Northport Loop West, Fremont, Calif. 94538. The sensor is designed with a pressure sensing element mounted on a ceramic substrate. A dielectric gel can be placed over the sensor element to provide electrical and fluid isolation. The sensor housing can have a Luer connection to couple to the endoscope 512. Further, the sensor body can have a pressure relief valve for redundant overpressure protection (not shown).

As can be understood from FIGS. 16 and 17, the pressure sensor 560 is attached to the endoscope 512 to communicate with a fluid channel extending through the endoscope shaft to the body cavity. The fluid channel or sensor channel 108b used by the pressure sensor 560 is independent of flow channel 108a used for distention fluid inflows into the body cavity. In the absence of fluid flows in the sensor channel 108b, the fluid in the channel 108b then forms a static column of incompressible fluid that changes in pressure as the pressure in the body cavity changes. With a sensor channel cross-section of 1 mm or more, the pressure within the pressure channel column and the pressure in the body cavity are equivalent. Thus, the pressure sensor 560 is capable of a direct measurement of pressure within the body cavity. In another variation shown schematically in FIG. 18, the pressure sensor 560 as indicated in FIG. 16 can consist of two independent sensing elements 560' and 560" that both interface with fluid extending into the sensor 560 from the single fluid channel 108b. The sensing elements 560' and 560" send pressure signals to controller 545 through cables 564' and 564" (FIG. 18). At the initiation of a procedure, or during a procedure, the controller then can be configured to monitor or compare pressure signals from the independent sensing elements 560' and 560". If the two sensors' pressure signals are not within a preselected range from one another, the controller 545 can provide a warning of sensor malfunction and/or terminate or modulate any ongoing operation of the fluid management system or resection device.

FIG. 17 schematically illustrates the fluid management system 500 in operation. The uterine cavity 502 is a potential space and needs to be distended to allow for hysteroscopic viewing. A selected pressure can be set in the controller 545, for example via a touch screen 565, which the physician knows from experience is suited for distending the cavity 502 and/or for performing a procedure. In one embodiment, the selected pressure can be any pressure between 0 and 150 mm Hg. In one system embodiment, the inflow pump 546A can operate as a variable speed pump that is actuated to provide a flow rate of up to 850 ml/min through first line or inflow line 550. In this embodiment, the outflow pump 546B can operate at a fixed speed to move fluid in the second line or outflow line 555. In use, the controller 545 can operate the pumps 546A and 546B at selected matching or non-matching speeds to increase, decrease or maintain the volume of distention fluid 244 in the uterine cavity 502. Thus, by independent control of the pumping rates of the inflow and outflow pumps 546A and 546B, a selected set pressure in the body cavity can be achieved and maintained in response to signals of actual intra-cavity pressure provided by sensor 560.

Figure 19:
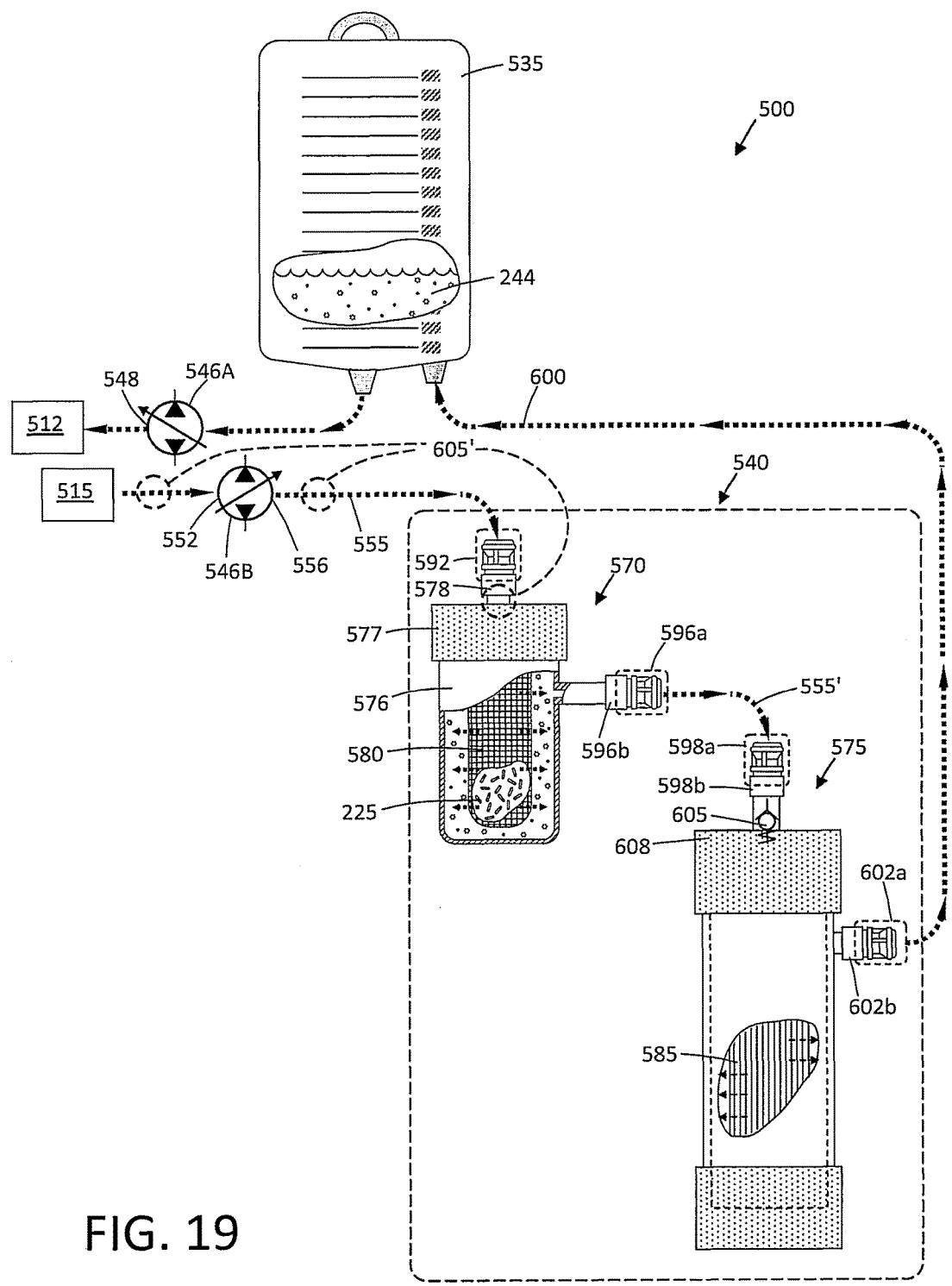
FIG. 19 is a cut-away schematic view of a filter module of the fluid management system of FIGS. 16-17.

In one system embodiment, as shown in FIGS. 17 and 19, the fluid management system 500 includes a filter module or system 540 that can include a first filter or tissue capturing filter 570 that is adapted to catch tissue strips 225 that have been resected and extracted from the body cavity 502. A second filter or molecular filter 575, typically a hollow fiber filter, is provided beyond the first filter 570, wherein the molecular filter 575 is adapted to remove blood and other body materials from the distention fluid 244. In particular, the molecular filter 575 is capable of removing red blood cells, hemoglobin, particulate matter, proteins, bacteria, viruses and the like from the distention fluid 244 so that endoscopic viewing of the body cavity is not obscured or clouded by any such blood components or other contaminants. As can be understood from FIGS. 16-19, the outflow pump 546B at its outflow side 556 provides a positive pressure relative to fluid flows into the filter module 540 to move the distention fluid 244 and body media through the first and second filters, 570 and 575, and in a circulatory flow back to the fluid source 535.

Referring to FIG. 19, in an embodiment, the first filter 570 comprises a container portion or vial 576 with a removable cap 577. The inflow of distention fluid 244 and body media flows though line portion 555 and through fitting 578 into a mesh sac or perforate structure 580 disposed in the interior chamber 582 of the vial 576. The pore size of the perforate structure 580 can range from about 200 microns to 10 microns. The lumen diameter of hollow fibers 585 in the second filter 575 can be from about 400 microns to 20 microns. In general, the pore size of perforate structure 580 in the first filter 570 is less than the diameter of the lumens of hollow fibers 585 in the second filter 575. In one embodiment, the pore size of the perforate structure 580 is 100 microns, and the lumen size of the hollow fibers 585 in the molecular filter 575 is 200 microns. In one embodiment, the molecular filter 575 is a Nephros DSU filter available from Nephros, Inc., 41 Grand Ave., River Edge, N.J. 07661. In one variation, the filter 575 is configured with hollow fibers having a nominal molecular weight limit (NMWL) of less than 50 kDa, 30 kDa or 20 kDa.

In another aspect of the invention, the molecular filter 575 is configured to filter large volumes of distention fluid, since the fluid flows are circulating. Additionally, the molecular filter 575 is configured to filter significant potential volumes of distention fluid that may contaminated with blood, blood products and the like that will be mixed with the fluid. In one embodiment, the molecular filter 575 has a membrane surface area of at least $0.6\ m^2$, $0.8\ m^2$, $1.0\ m^2$, $1.2\ m^2$ and $1.4\ m^2$, wherein the membrane surface area is defined as the total surface area of the lumens of the hollow fibers 585 in the molecular filter 575. In another aspect of the invention, a method of fluid management can include distending a body space and maintaining a flow rate of up to 850 ml/min of a distention fluid flow into and out of a body space and thereafter through a filter system 540 capable of removing at least 20 ml, 40 ml or 60 ml of blood from the distention fluid 244.

Referring to FIG. 19, it can be seen that the filter module 540 includes detachable connections between the various fluid flow lines to allow for rapid coupling and de-coupling of the filters and flow lines. More in particular, flow line 555 extending from the tissue resecting probe 515 has a connector portion 592 that connects to inlet fitting 578 in the first filter 546A. Flow line portion 555' that is intermediate the filters 546A and 546B has connector portion 596a that connects to outlet fitting 596b in first filter 542A. The outflow end of flow line 555' has connector 598a that connects to inlet fitting 598b of the second filter 546B. The return flow line 600 that is intermediate the second 546B and fluid source 535 has connector portion 602a that connects to outlet fitting 602b in second first filter 546B. In one embodiment, at least one check valve 605 is provided in the flow path intermediate the filters 546A, 546B which for example can be in line 555', connectors 596a, 598a or fittings 596b, 598b. In FIG. 19, a check valve 605 is integrated with the inlet end 608 of the second filter 546B. In use, the operation of the system will result in substantial fluid pressures in the interior of the second filter, and the check valve 605 allows for de-coupling the first filter without escape of pressure and release of fluid media into the environment, for example, when the tissue resecting procedure is completed and the physician or nurse wishes to transport the vial 576 and tissue strips 225 therein to a different site for biospy purposes. In general, a one-way valve such as check valve 605 can be provided at one or more locations in flow lines 555 and 555' to prevent back flows of pressure through line 555 to the resecting device 515. For example, a one-way valve 605', such as a float valve, can be provided at one or more locations in line 555 or fitting 578 as indicated by the dashed line in FIG. 19 (see also FIGS. 20-21). A float valve 605" can also be provided in line 550 proximate the saline source 535.

In one aspect, a fluid management system comprising a first fluid line 550 configured to carry distention fluid 224 from a fluid source 535 to a body space, a second fluid line 555, 555' and 560 configured to carry fluid from the body space to a first filter 570 and then to a second filter 575 and then back to the fluid source 535, an outflow pump operatively coupled to the second fluid line and at least one check valve 605 in the second fluid line intermediate the first and second filters 570 and 575.

In one embodiment, the controller 545 of the fluid management system 500 is configured for calculation of a fluid deficit that is measured as a difference between a fluid volume delivered to the body space 502 and a fluid volume recovered from the body space during a medical procedure such as fibroid removal (see FIGS. 16-19). A method of fluid management in a hysteroscopic procedure comprises providing a distention fluid source 535 (FIG. 17) having a predetermined volume, introducing fluid (e.g., saline) from the source 535 through a first flow line or inflow line 550 into the uterine cavity and through a second flow line or outflow line 555 out of the cavity into a filter module 540 and through a further portion 600 of the second flow line back to the fluid source 535 wherein the interior volume of the first and second flow lines and the filter module when subtracted from the predetermined volume of the source 535 equals 2.5 liters or less. The instructions for use then can include the requirement that only a single 3 liter saline bag can be used in any fibroid or polyp removal procedure, which in turn will insure that saline intravasation can never exceed 2.5 liters. In this variation, the predetermined volume of the source 535 can be 3.0 liters, as in a standard 3 liter saline bag, and the interior system volume can be at least 0.5 liters.

Figure 20:
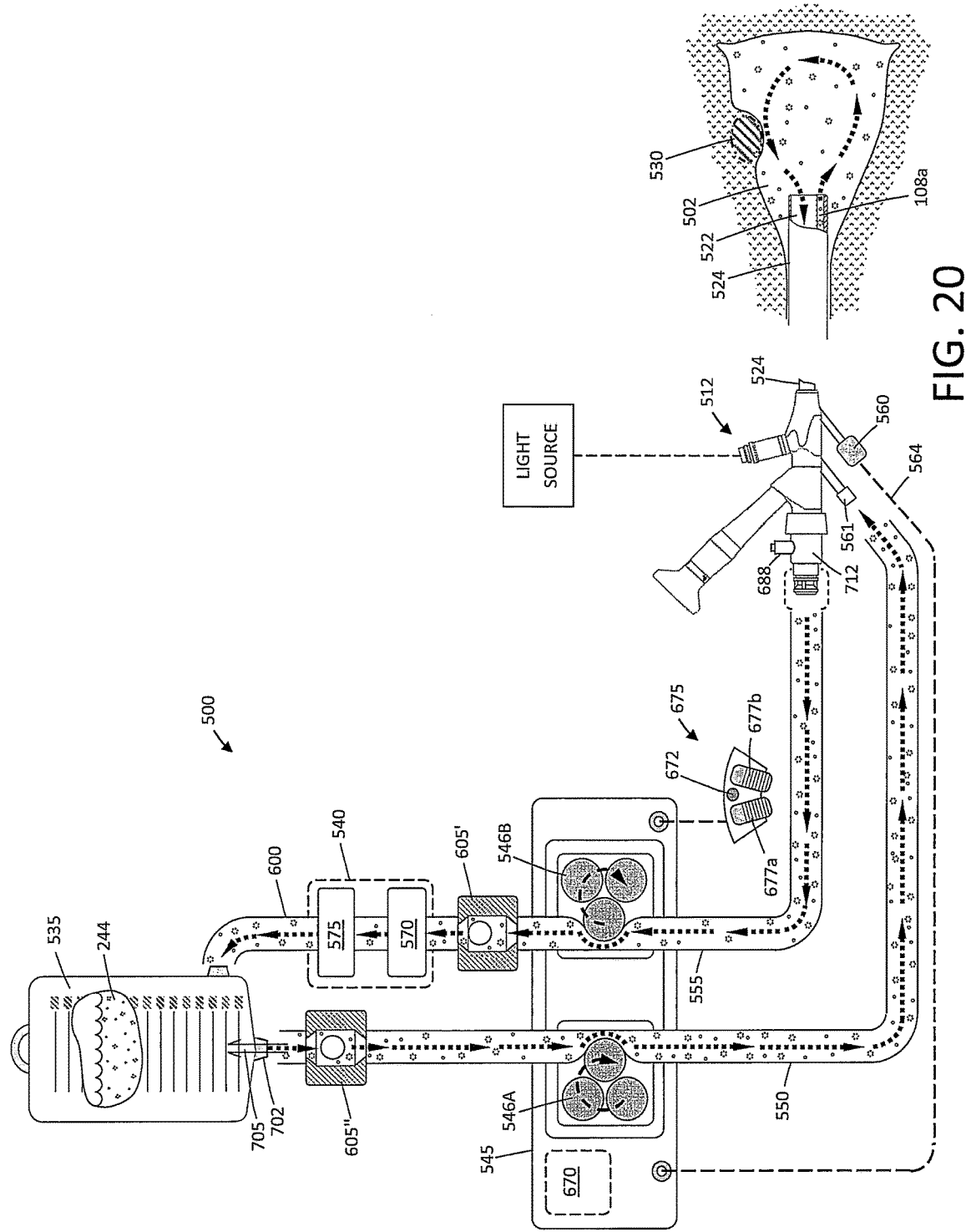
FIG. 20 is a schematic view of an endoscope and fluid management system being used in a diagnostic mode.
Figure 21:
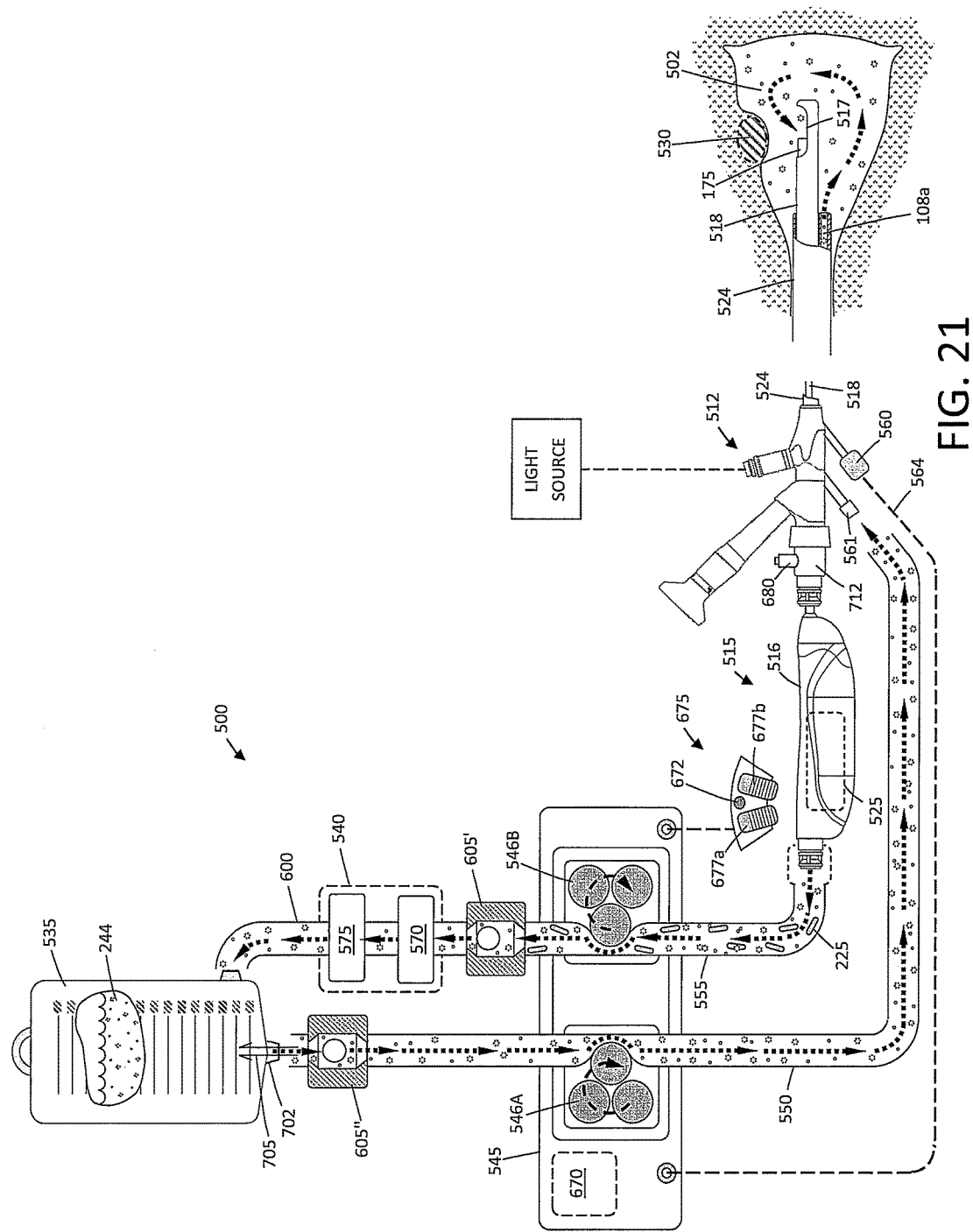
FIG. 21 is a schematic view of the endoscope and fluid management system of FIG. 20 together with a resecting probe with the assembly as used is a non-diagnostic or therapeutic mode.

FIGS. 20 and 21 are schematic diagrams relating to the integrated operation of an RF tissue resecting probe 515 of the type described above and a fluid management system 500 of the type described above. In general, the controller 545, RF generator 670 and fluid management system 500 are adapted to provide controlled flows of distention fluid into and out of a body cavity 502 while maintaining a targeted pressure within the body cavity while at the same providing RF energy delivery to the resecting probe contemporaneous with fluid flows. In one system embodiment, the system can operate in three different modes, all controlled by the controller 545: (i) a diagnostic mode for hysteroscopy, (ii) a resecting treatment mode for tissue resection and extraction; and (iii) and a coagulation treatment mode for tissue coagulation.

Referring to FIG. 20, in diagnostic mode, the inflow or infusion pump 546A, the outflow or aspiration pump 546B and the pressure sensor 560 and monitoring system are all activated. In one embodiment, the touchscreen 565 on controller 545 has a graphical user interface (GUI) with fluid control settings that can be adjusted by the physician (FIG. 16). The inflow pump 546A can be toggled ON/OFF by touching the inflow pump button on the GUI. The targeted intra-cavity pressure can be set on the touchscreen 565, for example from 0 to 150 mmHg or more (FIG. 16).

In a method of operation as shown in FIG. 20, the physician sets a target intra-cavity pressure on the GUI and then activates the inflow pump 546A which causes a flow of distention fluid 244 through the inflow or infusion line 550 and endoscope 512 into the body cavity 502. In one embodiment, the inflow pump 546A in diagnostic mode can be actuated on the touchscreen 565. In the diagnostic mode, the controller 545 is configured to not actuate the outflow pump 546B until the set pressure is attained or there is an overpressure condition. Thereafter, in one variation, the outflow pump 546A will then operate at a fixed rate and the inflow pump speed can be modulated in response to signals from the pressure sensor to stabilize the pressure around the targeted cavity pressure. The actual intra-cavity pressure measured by the pressure sensor 560 can be displayed on the controller GUI (FIG. 16).

In order to stabilize fluid pressure in a body cavity, the controller 545 includes a pressure control algorithm that is configured as a feedback control loop. The controller microprocessor reads both the intra-cavity pressure set point and the actual cavity pressure based on signals from the pressure sensor 560. In response to these two parameters, the algorithm calculates a delta value signal based on a generic proportional integral (PI) control algorithm. The delta value is sent to a digital to analog converter and fed into a motor amplifier that drives the inflow pump 546A. The controller algorithm then minimizes the difference between the set pressure and the actual pressure by adjusting the speed of the inflow (infusion) pump 546A.

In one embodiment, the system further includes an actuator and algorithm for providing a rapid fluid inflow and fluid outflow for flushing the body cavity 502, which for example can be an actuator button 672 on a footswitch assembly 675. In this flushing method, the outflow (aspiration) pump 546B is actuated to provide an increased level of outflow and then the pressure algorithm modulates the speed of the inflow (infusion) pump 564A to maintain the targeted pressure in the cavity. Thus, in the diagnostic mode, the system can be actuated to rapidly flush the body cavity with fluid inflows and outflows while the controller algorithm maintains intra-cavity pressure as described above. The flow rate through the system and body cavity can be pre-set at 100 ml/min or greater, for example at 200 ml/min or 300 ml/min. In another embodiment, the physician may select a rapid flow rate on the touchscreen from 200 ml/min to 800 ml/min.

In a non-diagnostic or therapeutic resecting mode for resecting tissue, referring to FIG. 21, the controller 545 delivers radiofrequency energy to the bi-polar electrode arrangement of the probe 515 (see FIGS. 12A-12C) to resect tissue and also actuates the two pumps to provide fluid inflows and outflows as described above. To operate in the resection mode, the physician can use the touchscreen 565 (FIG. 16) to enter a non-diagnostic (therapeutic) mode of operation. Thereafter, a first pedal 677a on the footswitch 675 can be used to actuate the system in resection mode to resect tissue. Actuation of the first pedal 677a results in the controller contemporaneously: (i) activating the outflow pump 546B at a fixed speed to provide outflows at a rate of 400 ml/min to 850 ml/min; (ii) activating the inflow pump 564A which has a rotation speed controlled and modulated by the controller 545 as described above to maintain a targeted pressure in the body cavity; (iii) delivering DC voltage to the motor 525 of the resecting probe 515 to reciprocate the resecting sleeve 175; and (iv) delivering RF energy to the bi-polar electrode arrangement of the resecting probe 515. In one embodiment, the RF generator 670 and controller 545 provide a variable DC voltage from 5-20 volts to the motor 525 of the resecting probe, a peak RF power of 200 watts, and a peak RF voltage of 240 volts at a 148 kHz frequency.

In the resection mode, the controller's pressure algorithm operates in a dynamic flow condition wherein the outflow of distention fluid 244 from the body cavity 502 varies as it will be dependent on the rate of tissue resection and the speed at which resected tissue strips 225 and fluid 244 can move through the extraction channel 160. The intra-cavity pressure is maintained at the set pressure by the feedback loop which operates in a similar manner as described above when the system operates in the diagnostic mode. Resected tissue strips 225 are moved through the system as described above and extracted from the body cavity and probe through the outflow line 555. The outflows of fluid carries resected tissue, blood and other body fluids into the first filter 570 and then the second filter 575 as can be seen in FIG. 21. When the physician releases pressure on the first pedal 677a, the resecting probe 515 is then de-activated and only the inflow 546A will remain active in controlling the intra-cavity pressure as described previously.

In the coagulation mode, the controller 545 and controller algorithm activates the bi-polar electrode arrangement of probe 515 to coagulate tissue and also to intermittently actuate the fluid flow functions as described above. The motor 525 in the probe handle is not activated, and the resecting sleeve 175 is positioned in an intermediate position in the window 517 in the outer sleeve 518 (cf. FIG. 12A). The intermediate position of the resecting sleeve 175 in the window 517 is a default position that occurs each time that DC current to probe motor 525 is terminated.

To initiate operation under the coagulation mode, it is assumed that the physician has previously selected the non-diagnostic (therapeutic) mode of operation using the touchscreen 565. The physician then can actuate a second pedal 677b on the footswitch 675 to coagulate tissue. Actuation of the second pedal 677b results in the controller contemporaneously: (i) delivering RF energy to the bi-polar electrode arrangement of the resecting probe 515; and (ii) intermittently actuating the inflow and outflow pumps 546A and 546B to cause a circulating fluid flow while maintaining intra-cavity pressure as described above. In one embodiment, the dual pumps operate for 1 to 8 seconds after a continuous interval of RF energy delivery for greater than 10 seconds. The fluid flow rate can be from 100 to 600 ml/min. Further, each time the physician terminates RF energy delivery, the inflow and outflow pumps 546A and 546B can be activated for 1 to 10 seconds. The intermittent circulating flows in the coagulation mode are adapted to aid in visualization and further to prevent heating of distention fluid 244 in the body cavity 502 as a result of the RF energy application. In one embodiment, the RF generator 670 and controller 545 provide bi-polar radiofrequency outputs for coagulation at a peak RF power of 110 watts and a peak voltage of 200 volts at a 148 kHz frequency.

In operating the system in any diagnostic or therapeutic mode, the controller 545 has an over-pressure protection algorithm in the event that pressure exceeds the targeted intra-cavity set pressure. In one embodiment, if the intra-cavity pressure exceeds the set pressure by a predetermined amount for a pre-selected time interval, then the controller 545 can activate the outflow pump 546B at a higher pumping rate than the inflow pump 546A until the measured fluid pressure in the cavity drops below the set pressure. Optionally, the controller 545 can slow or stop the inflow pump 546A until intra-cavity pressure drops to the targeted level. In one variation, the pump or pumps can be activated to reduce intra-cavity pressure if the measured pressure exceeds the set pressure by 5 mmHg for greater than 1 second, 2 seconds or 5 seconds.

Another mechanism for over-pressure protection is provided in the form a pressure relief valve 680 as depicted in FIG. 18. In one variation, the pressure relief valve 680 is coupled the housing 682 of sensor 560 and communicates with flow channel 108b' in the sensor 560 to allow fluid venting and pressure relief through the sensor body. The pressure relief valve 680 can relieve pressure at a suitable pressure greater than 100 mm Hg, for example 100 mm Hg, 125 mmHg, 150 mmHg or another predetermined pressure. Thus, if intra-cavity pressure exceeds the targeted maximum level, the controller 545 provides an algorithm-based pressure relief mechanism by modulating the pumps while the check-valve 680 provides a back-up form of pressure relief (FIG. 18). Further, the system can include a manual pressure relief valve 688 in a disposable fitting 712 coupled to the endoscope for additional safety redundancy (FIG. 20).

In another aspect of the invention, the controller 545 includes an algorithm that is adapted to de-activate a powered resection device in the event that the actual pressure in the treatment site drops below a predetermined threshold level. The controller 545 is provided with continuous signals of actual pressure in the site from the pressure sensor assembly 560 (FIG. 18). In one variation, if the actual pressure in the site drops below an allowable threshold pressure level, then the controller algorithm can automatically de-activate the motor that drives a reciprocating or rotating resecting member. In another variation, the controller algorithm can de-activate RF energy delivery to the working end of a resecting device 515 as shown in FIGS. 16-17. In this variation wherein RF energy delivery is de-activated, the algorithm may permit continued movement of the resecting sleeve 175 for a selected interval and then RF may be re-activated after the intra-cavity pressure level increases above the predetermined threshold either instantaneously or when such pressure exceeds the threshold level for a selected interval, for example of 1 to 10 seconds. In another variation, the controller algorithm can de-activate both the motor drive and RF delivery upon a fall in pressure below the threshold pressure level. The threshold pressure level in this algorithm can be any predetermined pressure, for example, 100 mmHg or less, 50 mmHg or less, or 25 mmHg or less. In one variation, the threshold pressure level is set at 15 mmHg.

In one aspect of the invention relating to treating tissue and directly sensing pressure in a body space, a method comprises (i) accessing a body space or potential body space with at least one system component configured to provide an inflow of distention fluid 244 to the space and an outflow of fluid from the space, the at least one component including an electrosurgical tissue resecting probe, (ii) providing a pressure sensor coupled to the at least one component configured to measure actual pressure in the space, (iii) sensing pressure within the space and modulating inflow and outflow rates in response to the sensed pressure to achieve or maintain a pressure set point in the space, and (iv) operating the electrosurgical probe at first RF parameters to resect tissue. The probe can be operated at second RF parameters to coagulate tissue. The step of modulating the inflow rates can provide inflows between 0 ml/min and 800 ml/min. The pressure set point can be between 30 mmHg and 200 mmHg. As described above, the step of sensing pressure is accomplished with a sensor coupled to an independent fluid channel that is separate from the flow channels carrying the distention fluid inflows and outflows.

In general, a fibroid treatment system corresponding to the invention comprises a controller, an inflow pump operated by the controller and configured to provide fluid inflow through a flow path to a patient's uterine cavity, an outflow pump operated by the controller and configured to provide fluid outflow through a flow path to the uterine cavity; and a motor driven resecting device operated by the controller. The resecting device comprise an elongate introducer having a tissue extraction channel (190A, 190B in FIG. 6A) therein with a diameter of no less than 2.4 mm and an outer sleeve 170 having a diameter of no more than 3.8 mm. The resecting device is adapted to remove fibroid tissue at a rate of at least 2 gm/min. In this variation, the controller can be configured to actuate the inflow and outflow pumps in response to signals of fluid pressure in the uterine cavity and to maintain the target pressure as described above. More in particular, the signal of fluid pressure can be provided by a pressure sensor coupled to a static fluid column communicating with the uterine cavity. In another variation, the controller can be configured to operate the resecting device in response to at least one parameter selected from a group consisting of an inflow pump speed, an outflow pump speed and signals of fluid pressure in the uterine cavity as will be described further below. In another aspect of the invention, a fluid management system 500 and cooperating electrosurgical probe are provided that include an inflow pump 546A configured for providing an inflow of a distention fluid into a site in a patient's body, a control system configured for operator selection of at least first and second flow control modes wherein the first flow control mode is configured for tissue resection and operates the inflow pump to provide a first peak inflow rate and wherein the second flow control mode is configured for tissue coagulation and operates the inflow pump to provide a second peak inflow rate. Typically, the first peak inflow rate is greater than the second peak inflow rate. In one variation, the first peak inflow is 1,000 ml/min, 800 ml/min, 600 ml/min or 500 ml/min. The fluid management and procedure system include a control system configured for operator-selection of a pressure set point at the site. As described above, the fluid management system and controller are configured to operate the inflow pump and an outflow pump to provide an outflow of distention fluid from the site to achieve or maintain the pressure set point in both the first and second flow control modes.

Referring to FIGS. 16-21, a fluid management system 500 of the invention comprises an inflow pump 546A configured for providing an inflow of a distention fluid 244 into a site in a patient's body and an outflow pump 546B configured for providing an outflow of fluid from the site, and a controller 545 configured for operator-selection of at least first, second and third flow control modes wherein the first flow control mode is configured for a diagnostic procedure and provides an inflow rate up to 800 ml/min, wherein the second flow control mode is configured for a tissue resection procedure and provides an inflow rate up to 1,000 ml/min, and wherein the third flow control mode is configured for a tissue coagulation and provides an inflow rate up to 800 ml/min with intermittent outflows at pre-selected time intervals.

Still referring to FIGS. 16-21, a fluid management and resection system corresponding to the invention comprises an elongated assembly configured for accessing and performing a procedure in a site in a patient's body, the system components including an endoscope, a tissue resecting probe, a fluid source and tubing set, inflow and outflow pumps and a controller wherein the inflow pump is configured for providing an inflow of fluid from the fluid source through a first channel in the assembly to the site, wherein the outflow pump is configured for providing an outflow of fluid through a second channel in the assembly from the site and wherein the controller is configured for contemporaneous control of the probe in at least one mode of operation and the inflow and outflow pumps to provide and maintain an operator-selected pressure set point at the site.

The system further includes a disposable pressure sensor detachably coupled to a system component, and in one variation, the pressure sensor is operatively coupled to a third channel in the system which typically is in the endoscope. In another variation, a pressure sensor is operatively coupled to the tubing set. Typically, the first channel described above is in the endoscope shaft 524 and the second channel is in the tissue resecting probe 515.

In another aspect of the invention, referring to FIGS. 20-21, the fluid management system includes a fluid source 535, typically a saline bag, with a sealed outflow port 702 and a inflow line tubing 550 that has a connector end 705 including at least one barb feature configured to permit said connector end 705 to advance into and spike the outflow port 702 but prevents withdrawal of said connector end 705 from the outflow port 702.

In another aspect of the invention, the fluid management system 500 (FIGS. 16-17) includes controller algorithms that are adapted to detect a significant fluid leak or loss within the system when deployed and in use in a diagnostic or therapeutic procedure. Such a leak can consist of fluid loss anywhere in the fluid path, such as at a connector in the inflow or outflow lines (550, 555) or through the cervical canal around the elongated shaft 524 of the endoscope 512 (see FIG. 17).

In order to determine a leak or fluid loss, a controller algorithm continuously monitors the input voltage to the motor of the inflow or infusion pump 546A wherein such input voltage corresponds directly to pump speed and thus corresponds to the fluid inflow rate. The algorithm further continuously monitors the input voltage to the motor of the outflow or aspiration pump 546B which corresponds directly the fluid outflow rate. During such continuous monitoring, if the algorithm determines that the inflow pump motor is operating at an input voltage (inflow rate) that exceeds a predetermined threshold voltage level, then a timer is started. The threshold voltage level is a function of the set pressure, the actual intra-cavity pressure and which of the operational modes in operation at the time (diagnostic mode, resection mode, etc.). In each of the operational modes, the input voltage of the outflow pump (outflow rate) is different to meet the objectives of each mode. Thus, for each different mode and corresponding outflow rate, a different threshold voltage, inflow rate and time interval is used to determine if there exists an unwanted fluid loss. In another variation, a controller algorithm can detect a leak or fluid loss in the system using a linear fit curve that relates infusion motor voltage to an elapsed time interval to signal the leak or fluid loss. This type of algorithm may allow for faster detection of a fluid loss in operating modes in which the inflow pump motor operates at higher speeds, such as in a resection mode. In other words, the fluid loss could be detected earlier in cases in which there is a higher rate of loss. Test data can be collected to measure fluid loss at different motor speeds over a time interval to develop such a linear fit curve.

If the timer exceeds a pre-selected time interval during which input voltage of the inflow pump motor exceeds the predetermined voltage threshold, the controller then will display a notification warning and/or audible or visual alarm to indicate a leak or fluid loss. The length of the pre-selected interval also can vary depending on the severity of the fluid inflow rate, that is, the input voltage to the inflow pump motor, in any of the system's operating modes. As the inflow rate increases above the nominal inflow rate in any mode, the time interval preceding the fluid loss warning or alarm will be decreased. In one variation, the predetermined voltage threshold level can correspond to inflow rates of at least 25 ml/min, at least 50 ml/min or at least 100 ml/min and the pre-selected time interval can be at least 1 second, at least 5 seconds or at least 10 seconds.

In another aspect of the invention, the controller 545 includes algorithms that are adapted to detect kinks or clogs in the infusion tubing of inflow line 550 or the aspiration tubing of outflow line 555. It is possible for the flexible tubing of either the inflow line 550 or outflow line 555 to be kinked which may remain temporarily unnoticed by the physician and the nursing staff. If the inflow line 550 is kinked, the decrease in fluid inflows into the treatment site will result in a loss of pressure in the site and the working space may collapse. A kink in the outflow line 555 can lead to an unwanted fluid pressure increase in the treatment site.

In order to rapidly detect a kink in the infusion line 550 on the positive pressure side of the inflow pump 564A, a controller algorithm is adapted to provide a kinked tubing warning if the calculated power driving the inflow pump motor exceeds a predetermined value over a pre-selected time interval. Such a predetermined value depends on the motor, gear box, pump head, and a predetermined pressure limit. As can be understood from the above description of the dual pump system, the motor power directly corresponds to the pressure on the positive pressure side of the inflow pump 564A. As the pressure in the inflow tubing increases as a result of a kink or clog in the tubing, the hydraulic load on the pump rollers from the tubing will increase, which transfers load to the inflow pump motor. This increase in load on the motor then results in an increase in the current which is required to drive the pump motor at the targeted speed. The controller 545 includes an algorithm for maintaining the pump speed (and corresponding flow rate) at a predetermined level, no matter the load, during use of the fluid management system in its various modes. The power value is measured by a controller algorithm, and at the predetermined limit, the algorithm can (i) display a warning of a blocked fluid flow which can relate to kinked tubing or a clog in the flow paths or filter 575; (ii) display a message or warning that the molecular filter 575 may be clogged; or (iii) display a message to exchange the filter 575. The algorithm can further interrupt the procedure by de-activating the pumps 546A, 546B, and/or by de-activating the power to any tissue-resecting device 515 in use.

The fluid management system 500 further includes a controller algorithm for detecting a kink or clog in the outflow line 555 on the negative pressure side of the outflow pump 546B. This kink detection is accomplished by monitoring the motor voltage of both pump motors. If the system is being operated in either the resection mode or diagnostic mode, the algorithm first checks to determine if the outflow pump 546B is in an ON state, and then checks that voltage applied to the inflow pump 546A. If the motor of inflow pump 546A is operating at a voltage below a predetermined threshold level, then a timer is started. The predetermined voltage threshold of the inflow pump motor is selected based on the expected input motor voltage during the resection and diagnostic modes. The typical fluid outflow rate from the uterine cavity during the resection and diagnostic modes is 250 to 500 ml/minute, a flow rate which requires a minimum motor voltage input on the inflow pump motor to maintain pressure. If the outflow from the uterine cavity decreases or stops as a result of a kink in the outflow line 555, then the actual intra-cavity pressure would remain at a relatively static level. In this static condition, the input voltage of the inflow pump motor would be below the predetermined threshold input voltage, and as such, the kink detection timer would be initiated. When the timer exceeds a pre-selected time interval ranging from 5 seconds to 120 seconds, the algorithm is adapted to provide a kinked tubing warning. Additionally, the algorithm can interrupt the procedure by de-activating the pumps (546A, 546B) and/or by de-activating the power to any resection device 515 in use.

The fluid management system 500 further includes a controller algorithm for detecting a kink in the tubing of outflow line 555 on the positive pressure side of the outflow pump 546B. The controller algorithm detects such a kink in the outflow line 555 if the measured motor current on the motor driving the outflow pump 546B exceeds a predetermined level. The predetermined level again depends on the motor, gear box, pump head, and a predetermined pressure limit. The motor current directly corresponds to the pressure on the positive pressure side of the pump 546B. As the pressure in the tubing increases (as a result of a tubing kink or a clogged filter) the hydraulic load onto the pump rollers from the tubing increases, which transfers load to the motor. This increase in load to the motor increases the current required to drive the motor at the targeted speed and flow rate. As described previously, the controller 545 includes an algorithm that maintains the pump speed at a predetermined level during use of the fluid management system in various modes. Thus, the kink detection algorithm measures the current that drives the outflow pump motor, and at the predetermined current limit over a pre-selected time interval, the algorithm can (i) display a warning of kinked tubing; (ii) display a message or warning that the molecular filter 575 is clogged; or (iii) display a message to exchange the filter 575. Additionally, the algorithm can automatically interrupt the procedure by de-activating the pumps (546A, 546B) and/or by de-activating the power to any resection device 515 in use in response to detection of the kinked tubing or clog in a flow path.

In another aspect of the invention, the controller 545 includes algorithms that are adapted to further control and optimize fluid pressure in a site during a tissue resection interval that uses a feedback control loop to maintain the targeted set pressure. The feedback control loop consists of utilizing the pressure sensor 560 to monitor actual pressure in the site, and then utilizing controller algorithms to modulate speeds of both the inflow pump 546A and the outflow pump 546B (FIG. 21). More in particular, when the physician initiates tissue resection with a tissue resecting device 515 as shown in FIGS. 16-17 and 21, the tissue volume interfacing the window 517 (FIG. 21) will at least partially block the window and thus begin to slow the fluid outflow through the extraction channel 160 in the inner sleeve 175. As a result of the reduction in outflow, signals from the pressure sensor 560 to the controller 545 will indicate an increase in actual pressure in the site, which then under previously described algorithms will cause a reduction in the input voltage in the inflow pump motor to thus slow down the fluid inflow rate. If the condition of reduced outflow continues for a first pre-selected time interval, the controller algorithm then will recognize that the resecting device is resecting tissue and sends a tissue-engagement signal to the controller. After a subsequent or second pre-selected time interval, the algorithm will cause the controller 545 to reduce the input voltage of the outflow pump motor (and fluid outflow rate) from a higher voltage level (e.g., 15 to 30 volt range) to a lower voltage (e.g., 5 to 12 volt range) and contemporaneously will put the inflow pump into a "ready" state. In this ready state, if a sudden decrease in actual pressure in the site were signaled by the pressure sensor 560, then the algorithm would cause delivery of a maximum voltage (e.g., 30 volts, instead of nominal voltage) to the inflow pump motor to thus cause the maximum fluid inflow into the site. Upon such a sudden decrease in pressure, the algorithm then sends a tissue-disengagement signal to the controller, which actuates the inflow pump at a maximum voltage as described above. In normal operating conditions, the nominal inflow pump voltage may be in the 10 to 20 volt range. The objective of this pressure maintenance algorithm is to anticipate a sudden decrease in pressure in the site when the window 517 in the resecting device is cleared of tissue while the resecting device is operating, or when tissue chips are cleared through the extraction channel 160 which then results in a rapid increase in outflow. The then ongoing decreased outflow pump voltage also reduces the outflow rate, and the "ready" state of the inflow pump insures that when the sudden tissue-clearing condition (tissue-disengagement signal) occurs, the inflow pump 546A is activated at its maximum voltage and inflow rate to match or exceed the outflow rate which then will prevent any drop in actual pressure in the site. The maximum inflow rate and the reduced outflow rate will continue until the targeted set pressure is maintained for a pre-selected interval that can range from 0.1 second to 10 seconds.

Another method of operating a fluid management system and RF resecting probe as depicted in FIGS. 16-21 comprises (i) accessing a site in a patient's body with a distal end of an endoscope and working end of an electrosurgical probe, (ii) delivering RF energy to the working end to apply energy to tissue at the site, (iii) contemporaneously operating a fluid management system to provide a selected rate of a fluid inflow to, and fluid outflow from, the site, (iv) detecting a change of a signal of an electrical parameter of the probe during operation and in response to detecting said change, switching at least one operational parameter of said fluid management system. Typically, the electrical parameter can include at least one of an impedance level, a power level, a voltage level and a current level. The operational parameter of the fluid management system that can be modulated includes at least one of a rate of fluid inflow to the site, a rate of fluid outflow through a system outflow channel from the site, a positive pressure level in communication with the fluid inflow channel, a negative pressure level in communication with the fluid outflow channel, a targeted pressure set point at the site and a rate of change of any of the preceding. In another variation, the at least one operational parameter can include an algorithm for operating a pressure sensing system configured to determine fluid pressure at the site. In the method described above, the applied energy can be adapted to ablate and resect tissue or to coagulate tissue.

While certain embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A fibroid treatment system, comprising:
   a controller;
   an inflow pump operated by the controller and configured to provide fluid inflow through a flow path to a patient's uterine cavity;
   an outflow pump operated by the controller and configured to provide fluid outflow through a flow path to the uterine cavity; and
   a motor driven resecting device operated by the controller, the device comprising an elongate introducer having (i) a tissue extraction channel therein with a diameter of no less than 2.4 mm and (ii) an outside diameter of no more than 3.8 mm such that the device is adapted to remove fibroid tissue at a rate of at least 2 gm/min;
   wherein the controller is configured to actuate the inflow and outflow pumps in response to signals of fluid pressure in the uterine cavity to maintain a target pressure therein;
   wherein said signal of fluid pressure in the site is provided by a pressure sensor coupled to a static fluid column communicating with the uterine cavity;
   wherein the pressure sensor includes two independent sensing elements that both interface with the static fluid column; and
   wherein the controller is configured to compare pressure signals from the two independent sensing elements of the pressure sensor and to provide a warning signal and/or turn off one or more of the inflow pump and the outflow pump if the pressure signals from the two independent sensing elements are not within a preselected range from one another.

2. The fibroid treatment system of claim 1, wherein the controller is configured to operate the resecting device in response to at least one parameter selected from a group consisting of an inflow pump speed, an outflow pump speed and signals of fluid pressure in the uterine cavity.

3. The fibroid treatment system of claim 1, wherein the controller is configured to provide a fluid loss signal in response to at least one parameter selected from a group consisting of an inflow pump speed, an outflow pump speed and signals of fluid pressure in the uterine cavity.

4. A fluid management system, comprising:
   a controller;
   a first pump operated by the controller and configured to provide fluid inflow to a site in patient's body;
   a second pump operated by the controller and configured to provide fluid outflow from the site in patient's body;
   wherein the controller is configured to provide at least one operating parameter selected from a group consisting of a first pump speed, a second pump speed, and a targeted pressure in the site rate; and
   wherein the controller is configured to provide a fluid loss warning if the first pump speed exceeds a predetermined level for a pre-selected time interval.

5. The fluid management system of claim 4 wherein the first pump speed provides a fluid loss warning at a first predetermined level when operating in a resection mode of operation and provides a fluid loss warning at a second predetermined level when operating in a non-resection mode of operation.

6. The fluid management system of claim 5 wherein the pre-selected time interval is at least 1 second.

7. The fluid management system of claim 5 wherein the pre-selected time interval is at least 5 seconds.

8. The fluid management system of claim 5 wherein the pre-selected time interval is at least 10 seconds.

9. The fluid management system of claim 5 wherein the controller is further configured to de-activate at least one pump if the first pump speed exceeds the predetermined level for the pre-selected time interval.

10. The fluid management system of claim 5 wherein the controller is further configured to de-activate a powered resecting device positioned in the site if the first pump speed exceeds the predetermined level for the pre-selected time interval.

11. A fluid management system, comprising:
    a controller;
    an inflow pump operated by the controller and adapted to provide a fluid inflow through a flow path to a site in a patient's body; and
    an outflow pump operated by the controller and adapted to provide a fluid outflow through a flow path from the site in the patient's body;
    wherein the controller is configured to provide at least one operating parameter selected from a group consisting of a first pump speed, a second pump speed, and a targeted pressure in the site; and wherein the controller is configured to provide a blocked flow warning if a calculated power for driving the inflow pump exceeds a predetermined level for a pre-selected time interval.

12. The fluid management system of claim 11 wherein the controller is further configured to de-activate at least one pump if the calculated power for driving the inflow pump exceeds the predetermined level for the pre-selected time interval.

13. The fluid management system of claim 11 wherein the controller is further configured to de-activate a powered resecting device positioned in the site if the calculated power for driving the inflow pump exceeds the predetermined level for the pre-selected time interval.

14. A fluid management system, comprising:
a controller;
a first pump operated by the controller and configured to provide fluid inflow to a site in patient's body;
a second pump operated by the controller and configured to provide fluid outflow from the site in patient's body;
wherein the controller is configured to provide at least one operating parameter selected from a group consisting of a first pump speed, a second pump speed, and a targeted pressure in the site; and
wherein the controller is configured to provide a blocked flow warning if an input voltage to the first pump is below a predetermined threshold voltage for a pre-selected time interval during which the second pump is operating.

15. The fluid management system of claim 14 wherein the pre-selected time interval ranges from 5 seconds to 120 seconds.

16. The fluid management system of claim 14 wherein the controller is further configured to de-activate at least one pump if the input voltage to the first pump falls below the predetermined level for the pre-selected time interval.

17. The fluid management system of claim 14 the controller is further configured to de-activate a powered resecting device positioned in the site if the voltage to the first pump exceeds the predetermined level for the pre-selected time interval.

18. A fluid management system, comprising:
a controller;
an inflow pump operated by the controller and configured to provide fluid inflow through a flow path to a site in patient's body;
an outflow pump operated by the controller and configured to provide fluid outflow through a flow path from the site in patient's body;
wherein the controller is configured to maintain at least one operating parameter selected from a group consisting of a first pump speed, a fluid inflow rate, a second pump speed, and a fluid outflow rate; and
wherein the controller is further configured to provide a blocked flow warning if a measured current to the outflow pump exceeds a predetermined threshold current for a pre-selected time interval.

19. A fluid management system for use in a tissue resection procedure, comprising:
a controller;
an inflow pump operated by the controller and configured to provide fluid inflow through a flow path to a site in patient's body;
an outflow pump operated by the controller and configured to provide fluid outflow through a flow path from the site in patient's body; and
a motor driven resecting device for resecting tissue at the site;
wherein the controller is configured to actuate an inflow pump and an outflow pump in response to signals of actual pressure at the site in the patient's body to provide respective fluid inflow and fluid outflow to maintain a target pressure at the site; and
wherein the controller is configured to de-activate the motor driven resecting device upon sensing that the actual pressure in the site falls below a predetermined threshold pressure level.

20. The fluid management system of claim 19 wherein the controller is further configured to de-activate a motor that drives the resecting device if actual pressure in the site falls below a predetermined threshold pressure level.

21. The fluid management system of claim 19 wherein the controller is further configured to de-activate at least one tissue resecting electrode if actual pressure in the site falls below a predetermined threshold pressure level.

22. The fluid management system of claim 19 wherein the threshold pressure level is 100 mmHg or less.

23. The fluid management system of claim 19 wherein the threshold pressure level is 50 mmHg or less.

24. The fluid management system of claim 19 wherein the threshold pressure level is 25 mmHg or less.

* * * * *